(12) United States Patent
Rajagopal et al.

(10) Patent No.: US 11,103,351 B2
(45) Date of Patent: Aug. 31, 2021

(54) TRANSCATHETER ATRIAL SEALING SKIRT AND RELATED METHOD

(71) Applicant: Opus Medical Therapies, LLC, Atlanta, GA (US)

(72) Inventors: Vivek Rajagopal, Atlanta, GA (US); Jaime Eduardo Sarabia, Mableton, GA (US); Yenchin Liao, Cary, NC (US)

(73) Assignee: Opus Medical Therapies, LLC, Atlanta, GA (US)

( * ) Notice: Subject to any disclaimer, the term of this patent is extended or adjusted under 35 U.S.C. 154(b) by 354 days.

(21) Appl. No.: 15/974,696

(22) Filed: May 9, 2018

(65) Prior Publication Data

US 2018/0289485 A1 Oct. 11, 2018

Related U.S. Application Data

(63) Continuation-in-part of application No. 15/943,971, filed on Apr. 3, 2018, now Pat. No. 10,820,992, and
(Continued)

(51) Int. Cl.
*A61F 2/24* (2006.01)

(52) U.S. Cl.
CPC .......... *A61F 2/2469* (2013.01); *A61F 2/2412* (2013.01); *A61F 2/2418* (2013.01); *A61F 2/2439* (2013.01); *A61F 2/2457* (2013.01); *A61F 2/2409* (2013.01); *A61F 2220/0075* (2013.01); *A61F 2230/008* (2013.01); *A61F 2230/0076* (2013.01); *A61F 2230/0078* (2013.01)

(58) Field of Classification Search
CPC .............. A61F 2/24–2466; A61F 2/011; A61F 2002/0072; A61F 2220/0008; A61B 17/0401–2017/0464
See application file for complete search history.

(56) References Cited

U.S. PATENT DOCUMENTS 4,242,715 A 12/1980 Laird
4,337,496 A 6/1982 Laird
(Continued)

FOREIGN PATENT DOCUMENTS

AU 2016202264 A1 11/2016
CA 3 059 102 A1 10/2018
(Continued)

OTHER PUBLICATIONS

International Search Report and Written Opinion in corresponding International application No. PCT/US2018/025971 dated Jul. 10, 2018.
(Continued)

*Primary Examiner* — Tan-Uyen T Ho
*Assistant Examiner* — Charles M Wei
(74) *Attorney, Agent, or Firm* — FisherBroyles, LLP; Rachel H. Huffstetler

(57) ABSTRACT

An atrial sealing skirt for transcatheter valves and an atrial sealing skirt with an integrated valve to reduce paravalvular regurgitation, with or without the presence of intracardiac leads. The atrial sealing skirt includes a top brim which is positioned to conform to the atrial floor at the deployment site.

29 Claims, 14 Drawing Sheets

Related U.S. Application Data a continuation-in-part of application No. 15/943,792, filed on Apr. 3, 2018, now Pat. No. 10,820,991.

(60) Provisional application No. 62/481,846, filed on Apr. 5, 2017, provisional application No. 62/509,587, filed on May 22, 2017, provisional application No. 62/558,315, filed on Sep. 13, 2017.

(56) References Cited

U.S. PATENT DOCUMENTS

| | | | |
|---|---|---|---|
| 4,746,057 A | 5/1988 | Wagner | |
| 4,830,360 A | 5/1989 | Carr, Jr. | |
| 5,079,776 A | 1/1992 | Crawford | |
| 5,312,438 A * | 5/1994 | Johnson | A61B 17/0401 606/104 |
| 5,569,306 A * | 10/1996 | Thai | A61F 2/0811 606/232 |
| 5,662,704 A * | 9/1997 | Gross | A61F 2/2412 623/2.1 |
| 5,683,451 A * | 11/1997 | Lenker | A61F 2/91 623/1.11 |
| 5,706,520 A | 1/1998 | Thornton et al. | |
| 5,849,004 A * | 12/1998 | Bramlet | A61B 17/0401 606/232 |
| 6,042,583 A * | 3/2000 | Thompson | A61B 17/06109 606/232 |
| 6,093,162 A | 7/2000 | Fairleigh et al. | |
| 7,530,995 B2 | 5/2009 | Quijano et al. | |
| 7,780,725 B2 | 8/2010 | Salahieh et al. | |
| 8,147,542 B2 * | 4/2012 | Maisano | A61B 17/0401 623/2.11 |
| 8,236,049 B2 | 8/2012 | Rowe et al. | |
| 8,252,050 B2 * | 8/2012 | Maisano | A61F 2/2457 623/2.11 |
| 8,273,973 B2 | 9/2012 | Kimmons et al. | |
| 8,333,155 B2 | 12/2012 | Cylvick | |
| 8,403,983 B2 | 3/2013 | Quadri et al. | |
| 8,449,599 B2 | 5/2013 | Chau | |
| 8,489,165 B2 | 7/2013 | Segman | |
| 8,545,553 B2 * | 10/2013 | Zipory | A61F 2/2451 623/2.37 |
| 8,549,175 B2 | 10/2013 | Krishna | |
| 8,690,939 B2 * | 4/2014 | Miller | A61F 2/2457 623/2.11 |
| 8,728,155 B2 | 5/2014 | Montorfano et al. | |
| 8,790,394 B2 * | 7/2014 | Miller | A61B 17/0401 623/2.1 |
| 8,888,843 B2 | 11/2014 | Khairkhahan et al. | |
| 8,900,295 B2 * | 12/2014 | Migliazza | A61B 17/0401 623/2.19 |
| 8,932,348 B2 | 1/2015 | Solem et al. | |
| 8,998,976 B2 | 4/2015 | Gregg et al. | |
| 9,005,084 B2 | 4/2015 | Silagy et al. | |
| 9,033,383 B2 | 5/2015 | Rampersad | |
| 9,034,033 B2 * | 5/2015 | McLean | A61F 2/2445 623/2.12 |
| 9,078,749 B2 | 7/2015 | Lutter et al. | |
| 9,375,312 B2 | 6/2016 | Weber | |
| 9,439,763 B2 | 9/2016 | Geist et al. | |
| 9,441,832 B2 | 9/2016 | Bushee | |
| 9,474,605 B2 | 10/2016 | Rowe et al. | |
| 9,480,559 B2 * | 11/2016 | Vidlund | A61L 27/3625 |
| 9,486,306 B2 | 11/2016 | Tegels et al. | |
| 9,578,982 B2 | 2/2017 | Rampersad | |
| 9,827,092 B2 * | 11/2017 | Vidlund | A61B 17/0401 |
| 9,849,001 B2 | 12/2017 | Thompson, Jr. et al. | |
| 9,895,221 B2 * | 2/2018 | Vidlund | A61F 2/2418 |
| 9,986,993 B2 * | 6/2018 | Vidlund | A61F 2/2457 |
| 10,039,639 B2 | 8/2018 | Marchand et al. | |
| 2004/0138707 A1 * | 7/2004 | Greenhalgh | A61B 17/0401 606/232 |
| 2004/0190383 A1 | 9/2004 | Marcucelli et al. | |
| 2005/0075727 A1 * | 4/2005 | Wheatley | A61F 2/2457 623/2.17 |
| 2005/0137697 A1 * | 6/2005 | Salahieh | A61F 2/2439 623/2.11 |
| 2006/0235509 A1 * | 10/2006 | Lafontaine | A61F 2/2436 623/2.11 |
| 2006/0241656 A1 | 10/2006 | Sterksen et al. | |
| 2006/0241745 A1 | 10/2006 | Solem | |
| 2007/0118151 A1 * | 5/2007 | Davidson | A61B 17/0625 606/144 |
| 2007/0142838 A1 * | 6/2007 | Jordan | A61B 17/0401 606/75 |
| 2007/0277279 A1 | 12/2007 | Battat | |
| 2008/0125860 A1 | 5/2008 | Webler | |
| 2009/0276040 A1 * | 11/2009 | Rowe | A61F 2/2454 623/2.18 |
| 2010/0016655 A1 * | 1/2010 | Annest | A61B 17/00234 600/37 |
| 2011/0004296 A1 * | 1/2011 | Lutter | A61F 2/2445 623/1.26 |
| 2011/0011917 A1 * | 1/2011 | Loulmet | A61B 17/0401 227/181.1 |
| 2011/0224785 A1 | 9/2011 | Hacohen | |
| 2011/0301698 A1 | 12/2011 | Miller et al. | |
| 2012/0078360 A1 | 3/2012 | Rafiee | |
| 2012/0136430 A1 | 5/2012 | Sochman et al. | |
| 2013/0023985 A1 * | 1/2013 | Khairkhahan | A61L 27/042 623/2.38 |
| 2013/0116780 A1 * | 5/2013 | Miller | A61F 2/2448 623/2.36 |
| 2013/0172978 A1 * | 7/2013 | Vidlund | A61F 2/2439 623/1.12 |
| 2013/0184811 A1 * | 7/2013 | Rowe | A61F 2/2418 623/2.11 |
| 2013/0190861 A1 | 7/2013 | Chau et al. | |
| 2013/0211508 A1 | 8/2013 | Lane et al. | |
| 2013/0282059 A1 | 10/2013 | Ketai et al. | |
| 2013/0282110 A1 | 10/2013 | Schweich, Jr. et al. | |
| 2013/0304197 A1 | 11/2013 | Buchbinder et al. | |
| 2013/0331929 A1 | 12/2013 | Mitra et al. | |
| 2014/0005778 A1 | 1/2014 | Buchbinder et al. | |
| 2014/0031928 A1 * | 1/2014 | Murphy | A61F 2/2418 623/2.18 |
| 2014/0163668 A1 | 6/2014 | Rafiee | |
| 2014/0296972 A1 | 10/2014 | Tegels et al. | |
| 2014/0316516 A1 | 10/2014 | Vidlund et al. | |
| 2014/0379076 A1 | 12/2014 | Vidlund et al. | |
| 2015/0142103 A1 | 5/2015 | Vidlund | |
| 2015/0250590 A1 | 9/2015 | Gries et al. | |
| 2015/0366556 A1 * | 12/2015 | Khairkhahan | A61B 17/0401 606/232 |
| 2015/0366666 A1 | 12/2015 | Khairkhahan et al. | |
| 2016/0022501 A1 | 1/2016 | Schultz et al. | |
| 2016/0120646 A1 | 5/2016 | Dwork et al. | |
| 2016/0213467 A1 | 7/2016 | Backus et al. | |
| 2016/0262878 A1 | 9/2016 | Backus et al. | |
| 2016/0262881 A1 * | 9/2016 | Schankereli | A61F 2/2418 |
| 2016/0310268 A1 * | 10/2016 | Oba | A61F 2/2418 |
| 2016/0317305 A1 | 11/2016 | Pelled et al. | |
| 2016/0324635 A1 | 11/2016 | Vidlund et al. | |
| 2016/0367360 A1 | 12/2016 | Cartledge et al. | |
| 2017/0143478 A1 | 5/2017 | Schwartz et al. | |
| 2017/0172737 A1 | 6/2017 | Kuetting et al. | |
| 2017/0209293 A1 | 7/2017 | Combs | |
| 2017/0227320 A1 | 8/2017 | Derousse | |
| 2017/0312078 A1 | 11/2017 | Krivoruchko | |
| 2018/0085215 A1 | 3/2018 | Vaturi et al. | |
| 2018/0289473 A1 * | 10/2018 | Rajagopal | A61F 2/2418 |
| 2018/0289474 A1 * | 10/2018 | Rajagopal | A61F 2/2418 |
| 2018/0289485 A1 * | 10/2018 | Rajagopal | A61F 2/2457 |
| 2018/0318071 A1 | 11/2018 | Lozonschi et al. | |

(56) References Cited

U.S. PATENT DOCUMENTS

| | | | | |
|---|---|---|---|---|
| 2019/0015205 | A1* | 1/2019 | Rajagopal | A61B 18/00 |
| 2020/0001135 | A1 | 1/2020 | Rajagopal | |

FOREIGN PATENT DOCUMENTS

| | | |
|---|---|---|
| CA | 3 059 106 A1 | 10/2018 |
| CN | 103826750 A | 5/2014 |
| CN | 105658178 B | 6/2016 |
| CN | 106618798 A1 | 5/2017 |
| DE | 10 2012 002 785 A1 | 8/2013 |
| EP | 1 462 880 A2 | 9/2004 |
| EP | 1 462 880 A3 | 4/2005 |
| EP | 3311774 A1 | 4/2018 |
| KR | 10-2020-0007805 A | 1/2020 |
| KR | 10-2020-0007806 A | 1/2020 |
| UY | 37667 A | 10/2018 |
| UY | 37668 A | 10/2018 |
| WO | 1994/020049 A1 | 9/1994 |
| WO | 2005/094711 A2 | 10/2005 |
| WO | WO2014021905 A1 | 2/2014 |
| WO | 2016050751 A1 | 4/2016 |
| WO | 2016168609 A1 | 10/2016 |
| WO | 2016/179427 A1 | 11/2016 |
| WO | 2016186909 A1 | 11/2016 |
| WO | DM/098 100 S | 6/2017 |
| WO | 2017/117560 A1 | 7/2017 |
| WO | 2018/187390 A1 | 10/2018 |
| WO | 2018/187495 A1 | 10/2018 |
| WO | 2020/005527 A1 | 1/2020 |

OTHER PUBLICATIONS

International Search Report and Written Opinion in corresponding International application No. PCT/PCT/US2018/026118 dated Jun. 15, 2018.
Toyama et al. Mitral annular motion in patients after transcatheter MitraClip and mitral valve surgery; Echocardiography 2017; 34: 334-339.
Boudjemline Y, Agnoletti G, Bonnet D, et al. Steps toward the percutaneous replacement of atrioventricular valves an experimental study. Journal of the American College of Cardiology 2005;46:360-5.
Bai Y, Chen HY, Zong GJ, et al. Percutaneous establishment of tricuspid regurgitation: an experimental model for transcatheter tricuspid valve replacement. Chinese medical journal 2010;123:806-9.
Laule M, Stangl V, Sanad W, Lembcke A, Baumann G, Stangl K. Percutaneous transfemoral management of severe secondary tricuspid regurgitation with Edwards Sapien XT bioprosthesis: first-in-man experience. Journal of the American College of Cardiology 2013;61:1929-31.
Lauten A, Doenst T, Hamadanchi A, Franz M, Figulla HR. Percutaneous bicaval valve implantation for transcatheter treatment of tricuspid regurgitation: clinical observations and 12-month follow-up. Circulation Cardiovascular interventions 2014;7:268-72.
Lauten A, Ferrari M, Hekmat K, et al. Heterotopic transcatheter tricuspid valve implantation: first-in-man application of a novel approach to tricuspid regurgitation. European heart journal 2011;32:1207-13.
Lauten A, Figulla HR, Unbehaun A, et al. Interventional Treatment of Severe Tricuspid Regurgitation: Early Clinical Experience in a Multicenter, Observational, First-in-Man Study. Circulation Cardiovascular interventions 2018;11:e006061.
Lauten A, Figulla HR, Willich C, et al. Percutaneous caval stent valve implantation: investigation of an interventional approach for treatment of tricuspid regurgitation. European heart journal 2010;31:1274-81.
Lauten A, Laube A, Schubert H, et al. Transcatheter treatment of tricuspid regurgitation by caval valve implantation—experimental evaluation of decellularized tissue valves in central venous position. Catheterization and cardiovascular interventions : official journal of the Society for Cardiac Angiography & Interventions 2014.
Figulla HR, Kiss K, Lauten A. Transcatheter interventions for tricuspid regurgitation—heterotopic technology: TricValve. EuroIntervention : journal of EuroPCR in collaboration with the Working Group on Interventional Cardiology of the European Society of Cardiology 2016;12:Y116-8.
Barbanti M, Ye J, Pasupati S, El-Gamel A, Webb JG. The Helio transcatheter aortic dock for patients with aortic regurgitation. EuroIntervention : journal of EuroPCR in collaboration with the Working Group on Interventional Cardiology of the European Society of Cardiology 2013;9 Suppl:S91-4.
Hahn RT, Meduri CU, Davidson CJ, et al. Early Feasibility Study of a Transcatheter Tricuspid Valve Annuloplasty: SCOUT Trial 30-Day Results. Journal of the American College of Cardiology 2017;69:1795-806.
Rosser BA, Taramasso M, Maisano F. Transcatheter interventions for tricuspid regurgitation: TriCinch (4Tech). EuroIntervention : journal of EuroPCR in collaboration with the Working Group on Interventional Cardiology of the European Society of Cardiology 2016;12:Y110-2.
Stephan von Bardeleben R, Tamm A, Emrich T, Munzel T, Schulz E. Percutaneous transvenous direct annuloplasty of a human tricuspid valve using the Valtech Cardioband. European heart journal 2017;38:690.
Kuwata S, Taramasso M, Nietlispach F, Maisano F. Transcatheter tricuspid valve repair toward a surgical standard: first-in-man report of direct annuloplasty with a cardioband device to treat severe functional tricuspid regurgitation. European heart journal 2017.
Rogers J. Transcatheter TR solution 6: Millipede. Transcatheter Cardiovascular Therapeutics; 2017 Nov. 1, 2017; Denver, Colorado.
Parada-Campelo F, Perlman G, Philippon F, et al. First-in-Man Experience of a Novel Transcatheter Repair System for Treating Severe Tricuspid Regurgitation Journal of the American College of Cardiology 2015;66:2475-83.
Nickenig G, Kowalski M, Hausleiter J, et al. Transcatheter Treatment of Severe Tricuspid Regurgitation With the Edge-to-Edge MitraClip Technique. Circulation 2017;135:1802-14.
Cao P. Catheter-Based Tricuspid Valve Replacement Via Right Atrium: An Animal Experimental Study. Transcatheter Cardiovascular Therapeutics; 2017; Denver, Colorado.
Navia JL, Kapadia S, Elgharably H, et al. First-in-Human Implantations of the NaviGate Bioprosthesis in a Severely Dilated Tricuspid Annulus and in a Failed Tricuspid Annuloplasty Ring. Circulation Cardiovascular interventions 2017;10.
Regueiro, et al. Transcatheter Mitral Valve Replacement: Insights From Early Clinical Experience and Future Challenges; JACC vol. 69, No. 17, 2017; May 2, 2017: 2175-92.
Non-Final Office Action received for U.S. Appl. No. 15/943,792 dated Jan. 8, 2020, 50 pages.
International Search Report and Written Opinion of the International Searching Authority dated Aug. 30, 2019, in International Application No. PCT/US19/36428.
Non-Final Office Action received for U.S. Appl. No. 15/943,971 dated Jan. 8, 2020, 49 pages.
International Search Report and Written Opinion issued in corresponding International Application No. PCT/US2019/057145 dated Dec. 31, 2019.
International Preliminary Report on Patentability received for PCT Application Serial No. PCT/US2018/025971 dated Oct. 17, 2019, 9 pages.
International Preliminary Report on Patentability received for PCT Application Serial No. PCT/US2018/026118 dated Oct. 17, 2019, 11 pages.
Supplementary European Search Report dated Apr. 30, 2021 in corresponding European Publication No. 3606443.
Supplementary European Search dated Mar. 21, 2019 in corresponding European Publication No. 3606444.

* cited by examiner

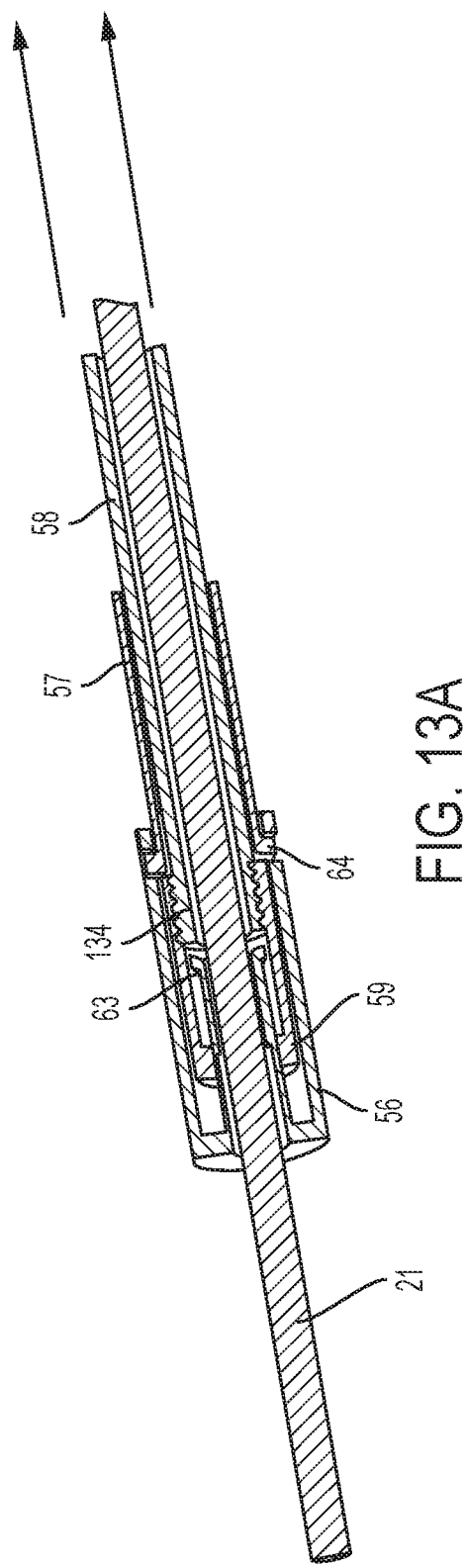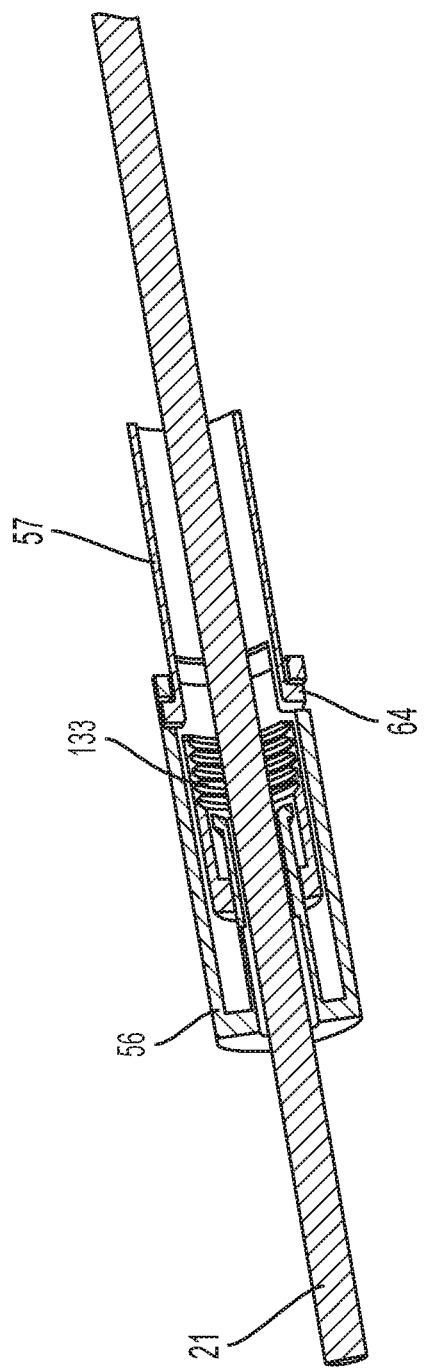
FIG. 13A
FIG. 13B

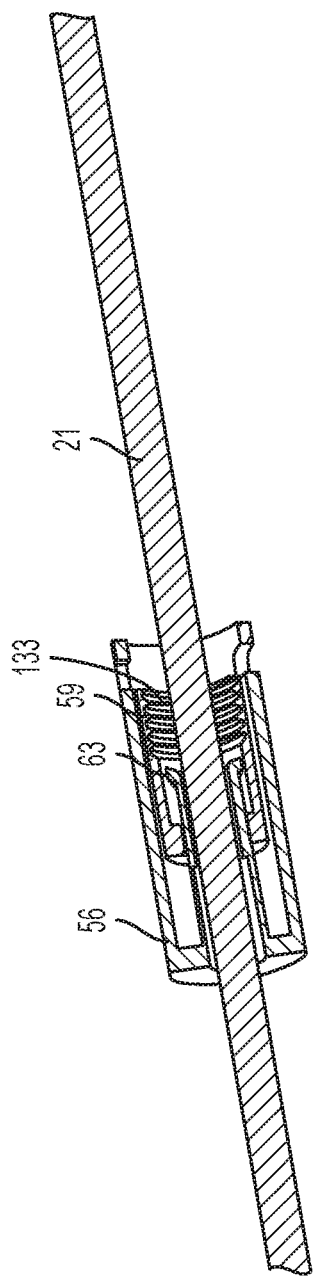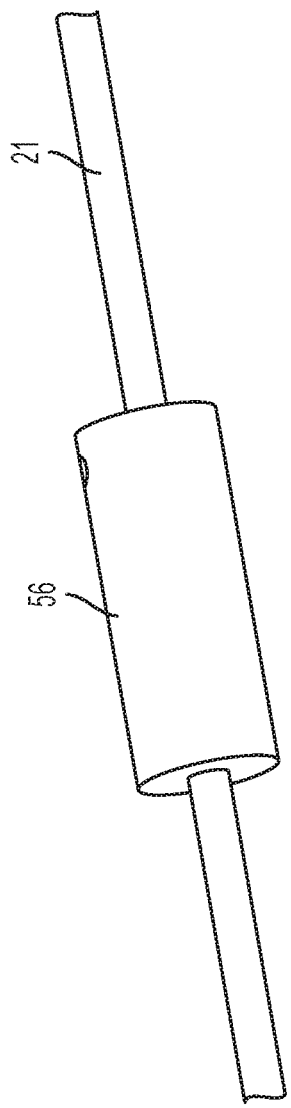

FIG. 17A - D

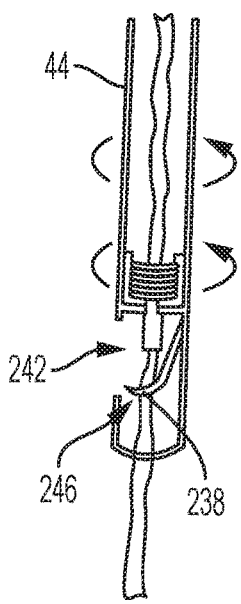 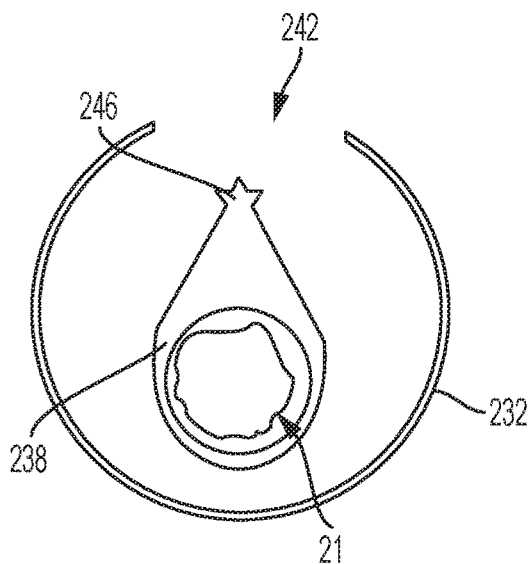
FIG. 19A          FIG. 19B
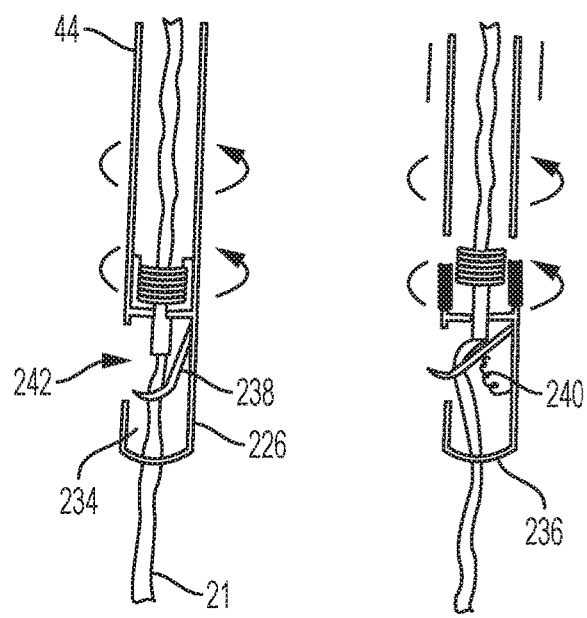 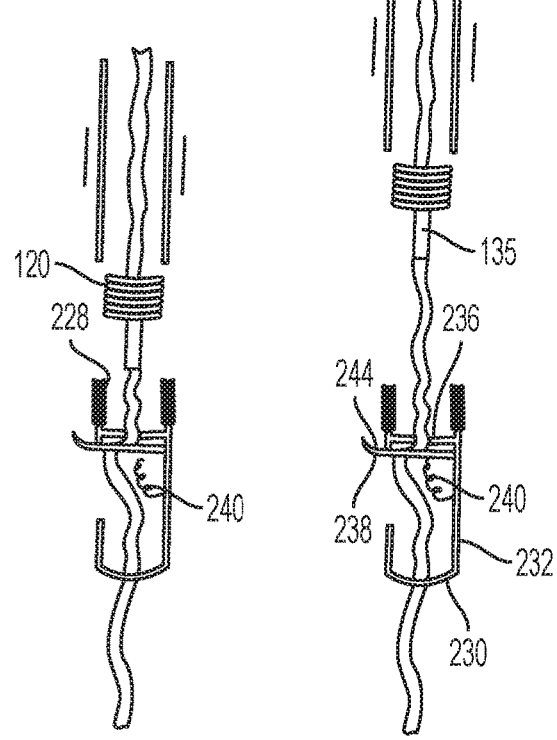
FIG. 20A - D

TRANSCATHETER ATRIAL SEALING SKIRT AND RELATED METHOD

CROSS REFERENCE TO RELATED APPLICATIONS

The application is a continuation-in-part of U.S. patent application Ser. No. 15/943,971 (Filed Apr. 3, 2018) and a continuation-in-part of U.S. patent application Ser. No. 15/943,792 (filed Apr. 3, 2018), both of which claim the benefit of and priority to Provisional Patent Applications Ser. Nos. 62/481,846 (filed Apr. 5, 2017), 62/509,587 (filed May 22, 2017), and 62/558,315 (filed Sep. 13, 2017), the disclosures of all are herein incorporated by reference.

FIELD OF THE INVENTION

The present invention relates generally to medical devices and systems that are implanted minimally invasively in the heart and methods of implantation of these devices and systems. More specifically, the invention pertains an atrial sealing skirt for transcatheter valves and an atrial sealing skirt with an integrated valve to reduce paravalvular regurgitation, with or without the presence of intracardiac leads.

BACKGROUND OF THE INVENTION

Transcatheter valves have proven safe and effective for the replacement of native cardiac valves. These valves have been tested extensively for replacement of aortic, mitral, and pulmonic valves, but replacement of tricuspid valves remains challenging given the complex and delicate anatomy to which prostheses must attach. Limiting paravalvular regurgitation of transcatheter mitral and tricuspid valves is challenging because the mitral and tricuspid annuli are complex saddle-shaped structures that are highly dynamic during the cardiac cycle. Compounding this difficulty for the tricuspid valve is the frequent presence of intracardiac leads in patients with significant tricuspid regurgitation (TR). Because ventricular leads traverse the annulus from the right atrium to the right ventricle, a transcatheter tricuspid valve must seal around both the annulus and the lead to limit regurgitation in these patients.

In patients receiving transcatheter aortic valve replacements (TAVR), investigators have developed technologies to mitigate paravalvular regurgitation, but these approaches have limitations, especially in the presence of intracardiac leads. In particular, balloon-expandable, mechanically-expandable, and self-expanding TAVRs have incorporated sealing membranes around their stent frames at the annular level to lessen paravalvular regurgitation. The sealing membranes consist either of polyethylene terephthalate, known as PET or Dacron, or of a porcine pericardial tissue wrap. These sealing membranes work by filling in the interstices between the outside of the TAVR and the aortic annulus, but this requires direct apposition of the valve against the annulus. For transcatheter tricuspid valves, direct apposition of the valve frame to the tricuspid annulus might not be desirable or feasible because unlike the aortic annulus, the tricuspid annulus is distensible, with minimal external support, and prone to injury. Additionally, sealing an intracardiac lead by trapping it between the valve frame and annulus would increase the risk of injury to the lead, which is undesirable.

Most transcatheter mitral valve replacements (TMVR) already use a similar mechanism to limit paravalvular regurgitation by trapping the base of the mitral leaflets between the valve frame and annulus. Thus, like the TAVR approach, the TMVR approach to lessen paravalvular regurgitation could damage the fragile tricuspid annulus, or damage intracardiac leads by trapping them between the valve frame and annulus. For example, the Medtronic Intrepid and NSCI Navigate valves anchor by either radial force against the annulus (Intrepid) or via annular "winglets" or hooks (Navigate). The CardiAQ-Edwards TMVR interacts directly with the annulus using a sub-annular clamping mechanism, while the Neovasc Tiara valve interacts indirectly via the fibrous trigones and also uses native leaflet engagement (both mechanisms could trap and injure leads). Three TMVR devices—Caisson, HighLife, and MValve—use an annular anchor as a docking system for the TMVR device, which would squeeze, and likely damage, any intracardiac lead between the anchor and the TMVR device.

Damage to intracardiac leads is not the only concern about the way TMVR devices mitigate paravalvular regurgitation. Because most TMVR devices reduce regurgitation by sealing the mitral annulus via direct anchoring to the annulus, these devices constrain, to varying degrees, freedom of mitral annular motion. Constraining this freedom might contribute to left ventricular dysfunction. For example, a study comparing transcatheter mitral valve repair (using Abbott Vascular's MitraClip device) to open heart surgery showed that mitral annular motion was significantly lower with open heart surgery, which the authors suggested was a factor in the lower left ventricular ejection fraction (LVEF) after open heart surgery compared to transcatheter repair. Similarly, a study comparing flexible to rigid mitral annuloplasty rings found a significantly lower LVEF with rigid rings, which constrain mitral annular motion more than flexible rings. Thus, in order to limit paravalvular regurgitation, current TMVR devices must anchor and constrain the mitral annulus, and this could have deleterious effects on left ventricular function.

To limit paravalvular regurgitation while avoiding constraint of the mitral annulus, the TMVR atrial skirts, by themselves, might lessen paravalvular regurgitation and seal around intracardiac leads; for example, the Medtronic Intrepid, Neovasc Tiara, and the Highlife TMVR devices have atrial skirts that lessen paravalvular regurgitation, and could facilitate sealing around intracardiac leads; however, without mitral annular anchoring used by these TMVR devices, all of these skirts suffer important limitations. The Neovasc Tiara atrial skirt suffers the biggest limitation by being asymmetrical to conform to the "D-shaped" mitral annulus and to the aorto-mitral curtain. This asymmetry is incompatible with the right atrial floor and tricuspid annulus. The skirts of the other TMVRs are symmetrical and are potentially compatible with the right atrial floor and tricuspid annulus, but these skirts lack the downward force and flexibility (along the perpendicular axis of the annulus) that are required for either reduction of paravalvular regurgitation or for sealing of intracardiac leads. Although Abbott Vascular Tendyne valve avoids annular anchoring by using an epicardial valve tether, its skirt also lacks the force and flexibility to seal around an intracardiac lead. The Tendyne valve skirt, like the skirts of other TMVR devices, consists of flexible interconnected wire loops covered with PET, and all these skirts assume a funnel shape with the wide top in the atrium and the narrow bottom at the valve annulus. These funnel-shaped skirts easily flex inwards and do not have any mechanism to increase outward and downward force of the atrial skirt differentially. For example, a mechanism to increase these forces in the skirt where it interacts with the lead would allow the skirt to control and constrain the lead.

The aforementioned atrial skirts do not have such a mechanism; therefore, a lead traversing the right atrium into the ventricle would not be constrained by the top of the skirt; instead, the lead would likely bow the skirt inward, creating a discontinuity of the skirt at the atrial floor, allowing paravalvular regurgitation.

Finally, another limitation of current atrial skirts is their fixation to their associated TMVR devices. It would be advantageous to be able to uncouple the atrial skirt from the valve; that is, to have the ability to place an atrial skirt first, followed by deployment of a transcatheter valve in the mitral or tricuspid space. Doing this would allow many combinations of atrial skirts and valves, which would maximize the ability to customize transcatheter valve placement and sealing depending on atrial, annular, and ventricular variations in anatomy.

Therefore, it is highly desirable to create a transcatheter valve skirt with several distinct features. One, its efficacy should be independent of mitral or tricuspid annular anchoring to avoid injuring annular anatomy or impairing ventricular function. Second, the skirt should be able to bend downwards with differential flexibility and force to conform to the local topography of the atrial floor, and to conform and seal around intracardiac leads. Finally, it would be advantageous to develop an atrial skirt that could be placed either as an integrated part of the transcatheter valve or independently of the transcatheter valve to facilitate the docking and sealing of pre-existing transcatheter valves to either the mitral or tricuspid annulus. Creating a skirt that can be independently placed and used as a docking system significantly expands the possibilities for treating patients suffering from mitral or tricuspid disease.

Applicant's Ser. No. 15/943,792 discloses a Transcatheter Anchor and Tether Devices, Systems and Methods of Implantation including an anchor delivery system for introducing a tether coupled to the anchor and a valve delivery system for delivering, positioning and sealing the valve. Applicant's Ser. No. 15/943,792 is directed to a Transcatheter Anchor and Tether Devices, Systems and Methods of Implantation wherein, the anchor delivery system comprises an anchor which is implanted and not initially coupled to a tether. The disclosure presented herein may be used in connection with either of these delivery or anchoring systems, or any delivery or anchoring systems.

SUMMARY OF THE INVENTION

The application relates to an atrial sealing skirt, which may be used as part of medical devices and systems, to be minimally invasively implanted in the heart to replace the native valve. More specifically, the application relates to a sealing skirt which may be endovascularly introduced. The sealing skirt may be secured within the heart by any securing means, anchoring means and/or tethering means including, by way of example, according to application Ser. Nos. 15/943,792 and/or 15/943,971. The sealing skirt may include an integrated valve or serve as a receptacle for receiving a separate valve. The sealing skirt may be introduced to a deployment site by known methods, including those described in the aforementioned applications. In one aspect, whether or not the atrial skirt is integrated with the valve, the system comprises an atrial sealing skirt configured to secure to the atrial floor and at least one tether configured to couple and/or secure the atrial sealing skirt to any intracardiac wall via the tether's interaction with an anchor.

In one aspect, the atrial sealing skirt is self-expanding and composed of nitinol and covered with either synthetic materials such as, but not limited to, polytetrafluoroethylene (PTFE) or polyethylene terephthalate (PET), or biological membranes such as, but not limited to, bovine or porcine pericardial tissue. In one aspect, the membrane covering the atrial skirt has a diameter greater than the annulus at the site of apposition so that in use the membrane substantially covers the mitral or tricuspid annulus.

The frame of the atrial skirt begins as a cylindrical shape, with the bottom of the cylinder at or below the valve annular level, and with the top of the cylinder extending into the atrium. From the top of the cylinder extends a top brim, composed of one or more wire extensions, made of laser-cut or formed nitinol. These extensions are fashioned as shapes such as, but not limited to, lines, arcs, hooks, circles, ellipses, sinusoidal curves, or of polygons of three or more sides. The extensions of the top brim, like the body of the skirt, are covered and/or connected with synthetic or biological membranes. The top brim is perpendicular to the atrial skirt body, or may bend toward the atrial floor as either as a convex or concave curve. To facilitate sealing as the top brim bends toward the atrial floor, the covering fabric consists of either a braided or knit fabric, which allows for "stretchability", improving the ability to conform to the topography of the atrial floor and wrap around any intracardiac leads.

In one aspect, adjacent to the top brim, running longitudinally along the interior or exterior of skirt body, are one or more conduits, which take the shape of a cylinder whose cross-section is any portion of a circle, ellipse, parabola, or hyperbola, or take the shape of a polyhedron with a flat base and top which assume the shape of a polygon with three or more sides. These conduits are constructed from the membrane covering the skirt, or may be made of, but not limited to, stainless steel, nitinol or other metal alloys. The one or more conduits are hollow and accommodate at least one cord attached to at least one tether, and each conduit attaches to a detachable lock near the atrial surface of the skirt.

The atrial sealing skirt further comprises at least one atrial positioning rod whose distal end is reversibly coupled to a detachable lock, which is attached to the proximal end of the conduit of the atrial skirt. By interacting with parts of a tethering or anchoring system, the positioning rod pushes or pulls the atrial skirt, thereby applying differential force and flexion to the associated top brim, allowing apposition to the atrial floor and/or conformation around an intracardiac lead. In another aspect, rotation of the positioning rod and/or pushing or pulling of internal elements of the positioning rod causes the detachable lock to lock, securing the atrial skirt, maintaining the force and flexion of the atrial skirt to atrial floor and/or intracardiac lead.

Other apparatuses, methods, systems, features, and advantages of the medical devices and systems that are implanted minimally invasively in the heart will be or become apparent to one with skill in the art upon examination of the following figures and detailed description. It is intended that all such additional apparatuses, methods, systems, features, and advantages be included within this description, be within the scope of the medical devices and systems that are implanted minimally invasively in the heart, and be protected by the accompanying claims.

BRIEF DESCRIPTION OF THE DRAWINGS

FIG. 13A is a cross-sectional side view of the locking system for atrial sealing skirt positioning in an un-locked position;

FIG. 13B is a cross-sectional side view of the locking system for atrial sealing skirt positioning in an interim position;

FIG. 14A is a partially cut away view of the locking system in the locked position;

FIG. 14B is a perspective view of the locking systems;

FIGS. 17A-17D are progressive, elevational views illustrating the operation of the atrial lock of FIG. 16A;

FIG. 19A is an elevational view of the atrial lock of FIG. 18;

FIG. 19B is a cross-sectional view of the atrial lock of FIG. 19A;

FIGS. 20A-20D are progressive, elevational views illustrating the operation of the atrial lock.

DETAILED DESCRIPTION OF THE INVENTION

The present invention can be understood more readily by reference to the following detailed description, examples, and claims, and their previous and following description. Before the present system, devices, and/or methods are disclosed and described, it is to be understood that this invention is not limited to the specific systems, devices, and/or methods disclosed unless otherwise specified, as such can, of course, vary. It is also to be understood that the terminology used herein is for the purpose of describing particular aspects only and is not intended to be limiting.

Figure 1:
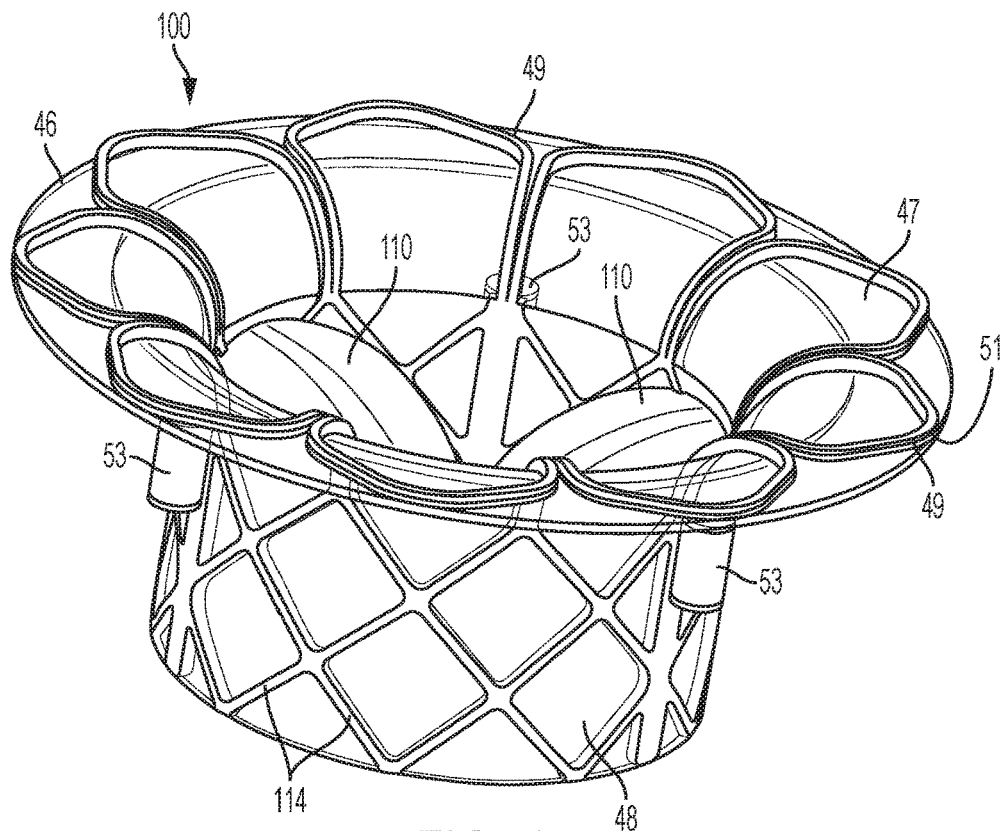
FIG. 1 is a perspective view of an atrial sealing skirt with an integrated valve.
Figure 6:
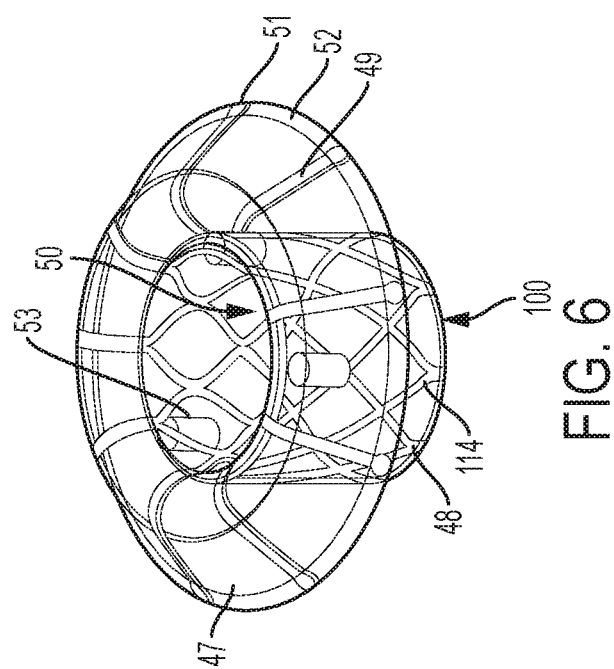
FIG. 6 is a top perspective view of FIG. 5.
Figure 8:
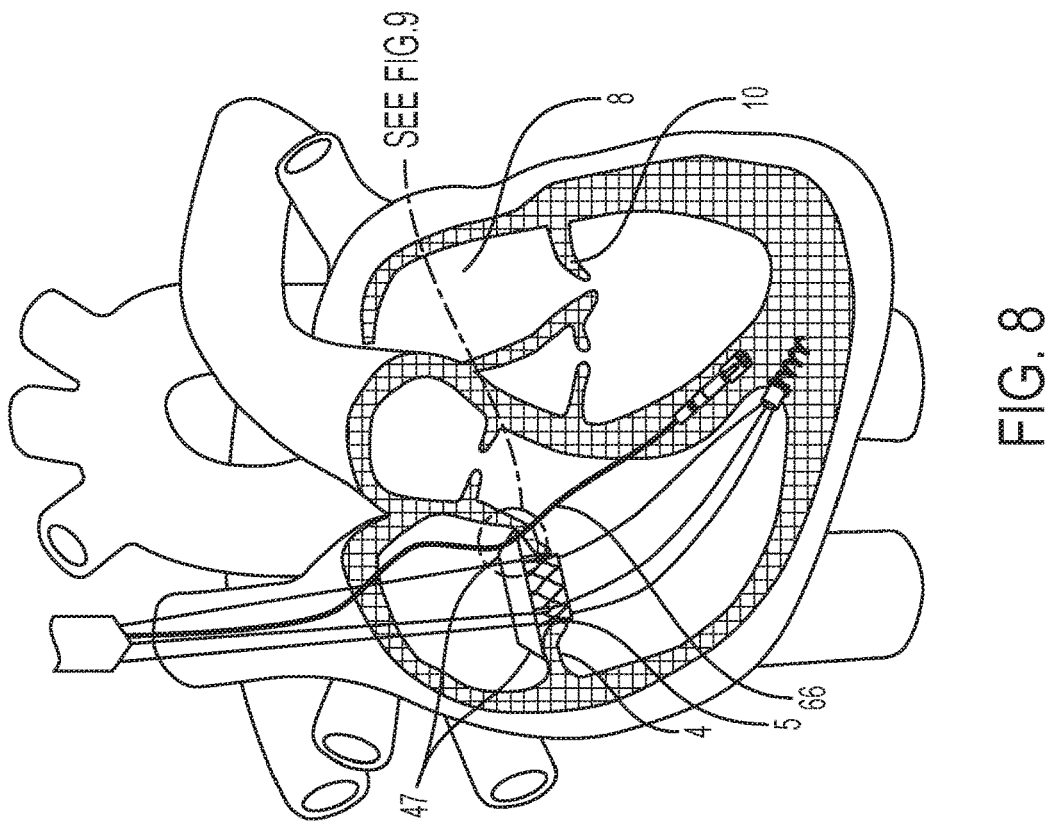
FIG. 8 is a cut-away view of the heart showing the atrial sealing skirt conforming to the atrial floor and sealing around an intracardiac lead.
Figure 11:
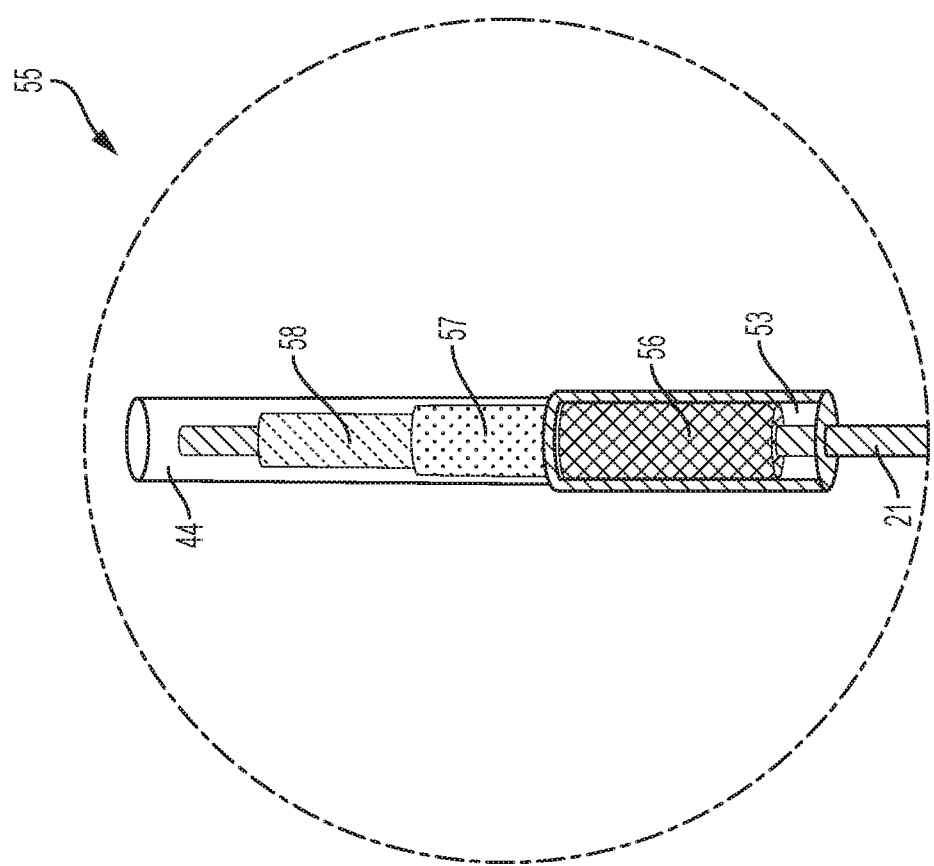
FIG. 11 is an enlarged side elevational view of the locking system.
Figure 10:
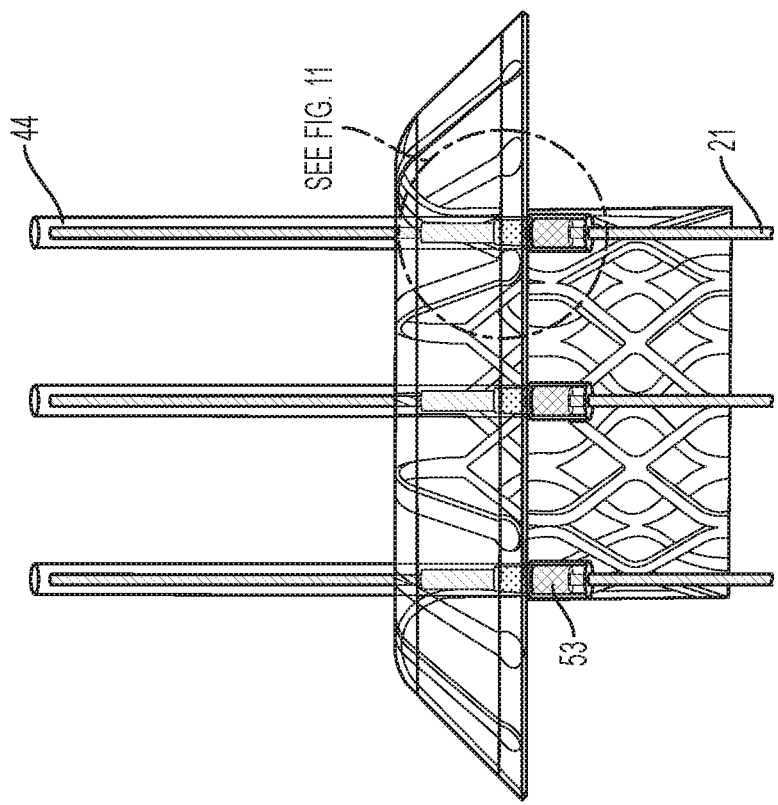
FIG. 10 is an enlarged side elevational view of the atrial sealing skirt coupled to atrial positioning rods and cords.
Figure 12A:
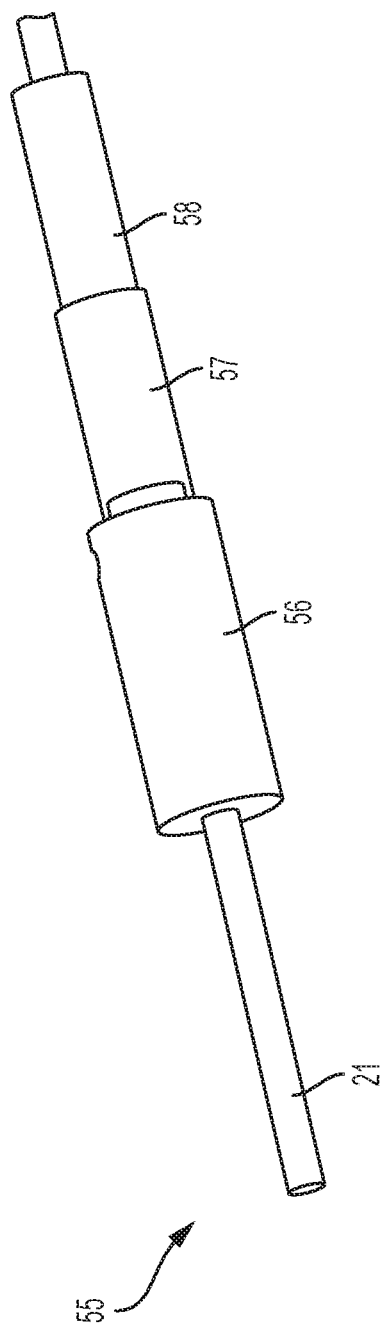
FIG. 12A is a perspective view of the locking system.
Figure 12B:
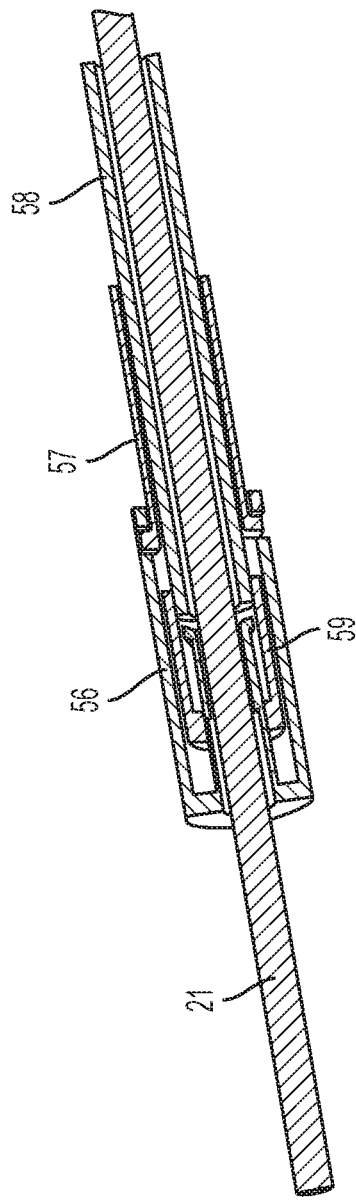
FIG. 12B is a perspective cut-away view of FIG. 12A.

As shown in the various Figures, the atrial sealing skirt 46 includes a skirt top brim 47 and a generally cylindrical atrial skirt body 48. The skirt top brim 47 extends circumferentially along the upper end of the skirt body 48. The atrial skirt top brim 47 which is configured to conform to an atrial floor 4, such as the right atrial floor as shown in FIG. 8. The skirt top brim 47, according to one aspect, includes an aperture as shown in FIGS. 6 and 10 which coincides in positioning and defines the open upper end of the conduit 53. As shown in FIG. 1, according to another aspect, the skirt top brim 47 does not include an aperture.

As used herein, the singular forms "a," "an" and "the" include plural referents unless the context clearly dictates otherwise. Thus, for example, reference to a "tether" includes aspects having two or more tethers unless the context clearly indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

As shown in the various Figures, the atrial sealing skirt 46 includes a skirt top brim 47 and a generally cylindrical atrial skirt body 48. The skirt top brim 47 extends circumferentially along the upper end of the skirt body 48. The atrial skirt top brim 47 which is configured to conform to an atrial floor 4, such as the right atrial floor as shown in FIG. 8.

Figure 3:
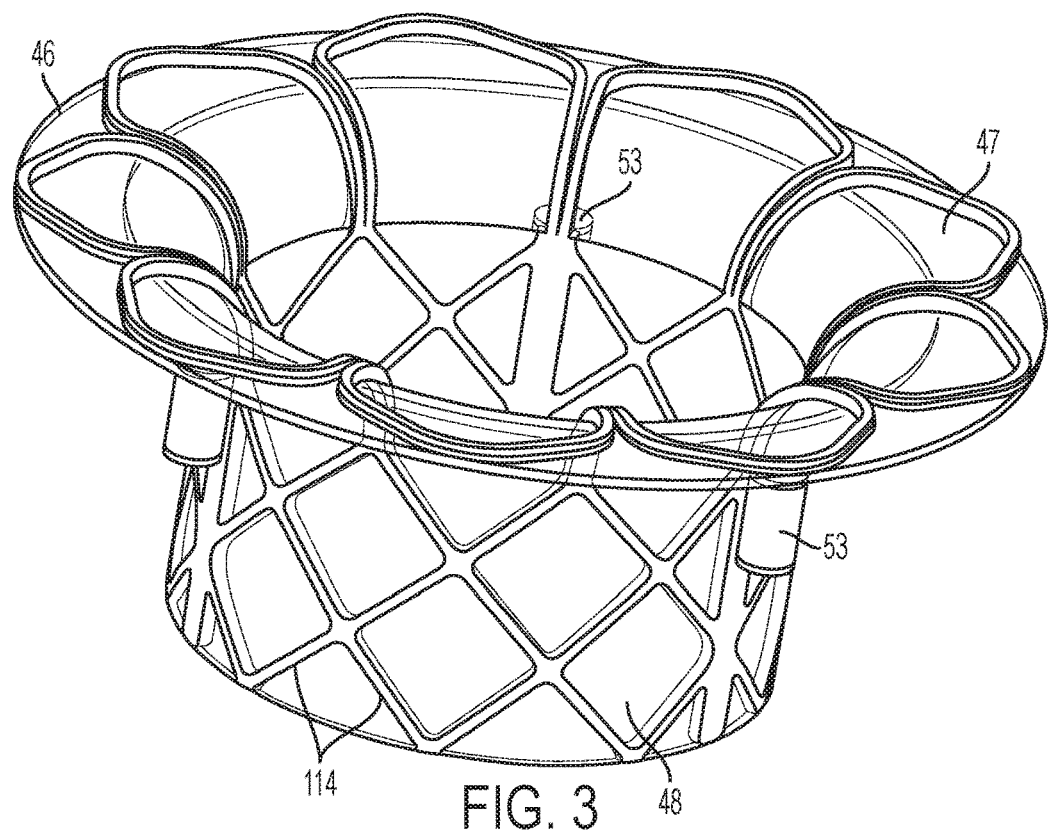
FIG. 3 is a perspective view of an atrial sealing skirt for receiving a valve.
Figure 4:
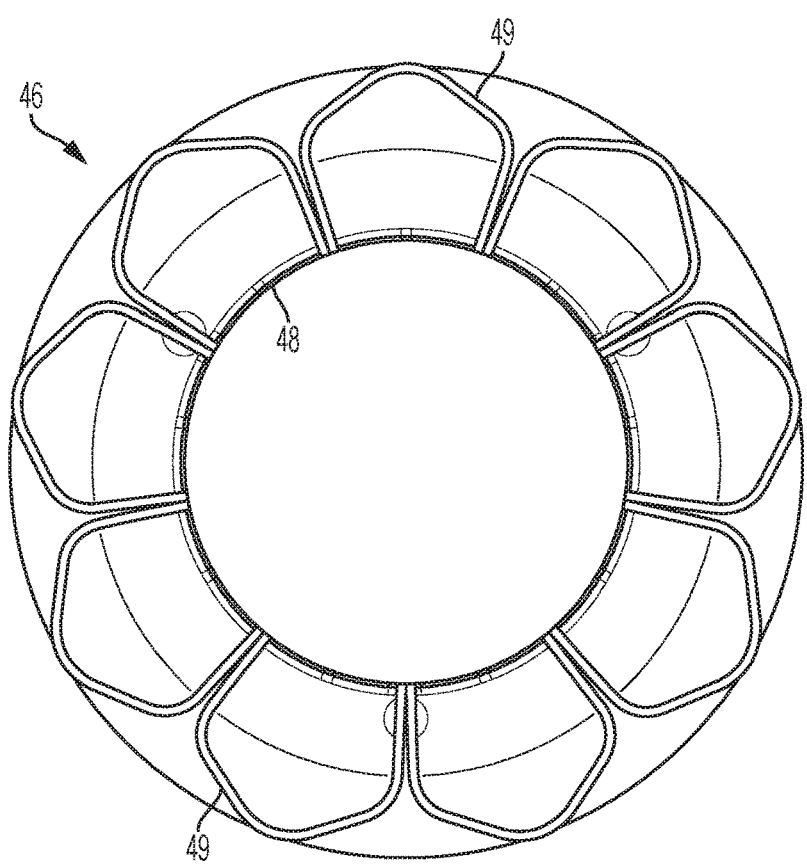
FIG. 4 is a top plan view of FIG. 3.
Figure 7:
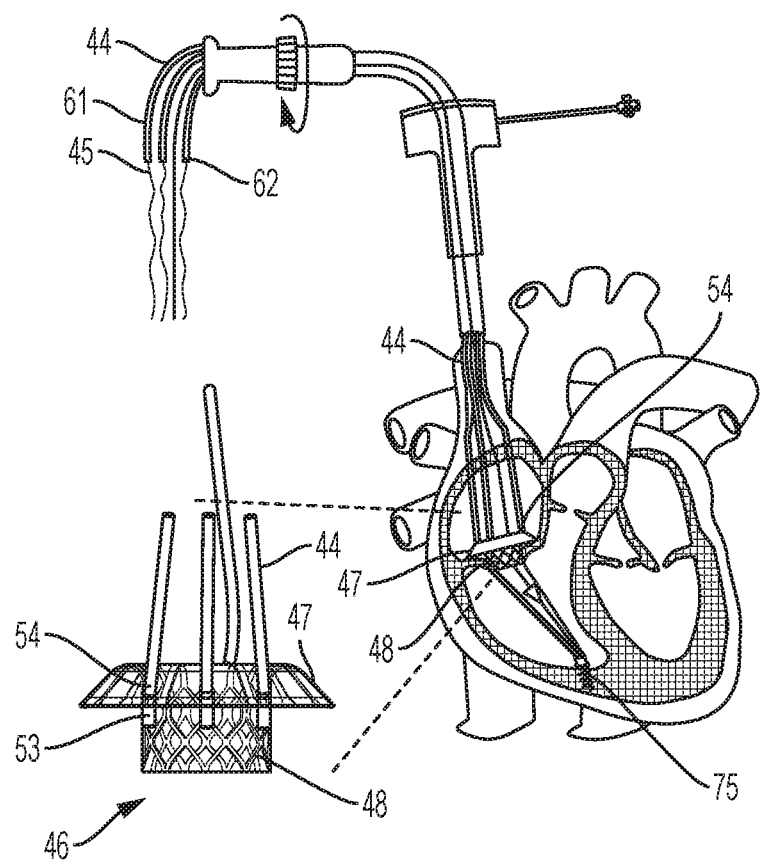
FIG. 7 is a perspective view of the atrial sealing skirt being positioned onto the right atrial floor by atrial positioning rods.

The transcatheter atrial sealing skirt 46 is sized and configured to sit in the tricuspid valve (in the example shown) between the right atrium and the right ventricle as illustrated in FIG. 7. The sealing skirt 46 may be pre-assembled with valve leaflets 110 as an integrated valve 100 (FIGS. 1 and 2) or the sealing skirt 46 may be constructed without valve leaflets and serve as a docking system for a separate transcatheter valve (FIGS. 3 and 4). This is by way of example. Optionally, however, with slight variations, the valve is sized and configured to be positioned in the mitral annulus between the left atrium and the left ventricle. Accordingly, then, with slight variations, these devices, systems, and methods are used for either the tricuspid or mitral valves and may be endovascularly placed by a venous structure including, but not limited to, either internal jugular vein, either subclavian vein, either subclavian vein or either femoral vein.

The atrial sealing skirt 46 is self-expanding (i.e. the skirt is compressible so that it fits through a catheter of system 1) and composed of nitinol, but may also contain elements made of, but not limited to, stainless steel, nitinol or other metal alloys. In another aspect, the atrial sealing skirt has a lower diameter that is smaller than or approximately equal to the annulus at the site deployment 5 (tricuspid annulus) or site deployment 10 (mitral annulus), thereby preventing or reducing apposition to the fragile tricuspid annulus, and preventing or reducing constraint of the mitral annulus.

At least one conduit 53 is defined in the outer wall of the atrial sealing skirt 46. Each conduit 53 is sized and shaped so that a portion of a cord 21 of a tethering or other securing system extends through the conduit 53, thereby connecting a tethering or other anchoring system to the atrial sealing skirt 46, allowing free movement until the skirt 46 is locked in place. In a further aspect, the atrial sealing skirt 46 has anchoring elements (not shown) positioned along its outer diameter. These anchoring elements allow fixation to the tricuspid or mitral annulus and/or leaflets, but are not necessarily used a primary fixation mechanism. In use, described more fully below, a central portion of the cord 21 (between the distal end and the proximal end) extends through and/or be coupled to the atrial sealing skirt 46 to hold the skirt in the desired position relative to the tricuspid annulus or the mitral annulus.

Figure 2:
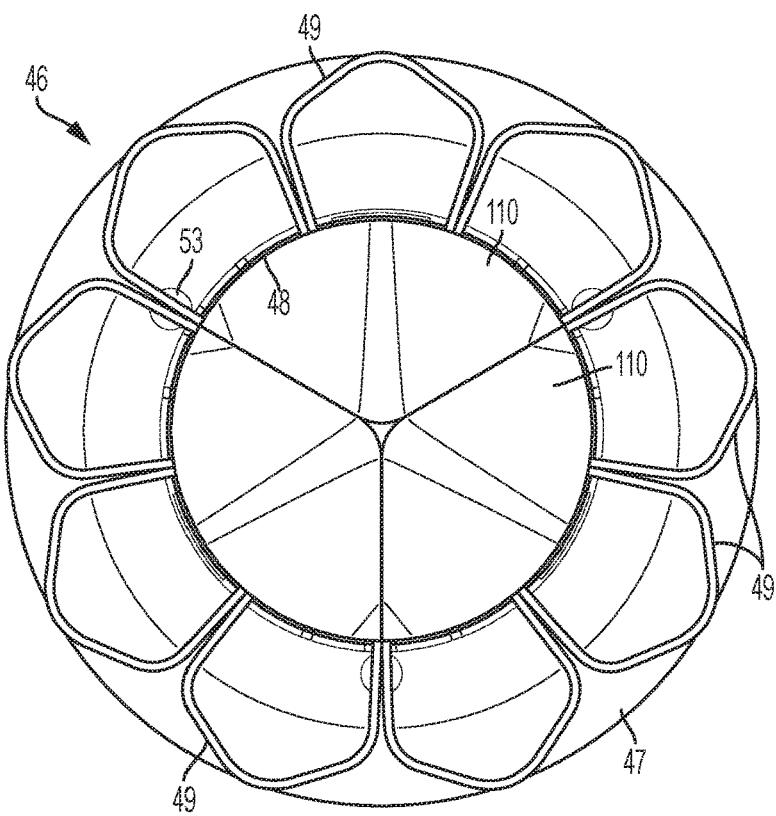
FIG. 2 is a top plan view of FIG. 1.

The sealing skirt 46 is an integrated valve 100 shown in FIGS. 1 and 2, composed of leaflets 110 extending radially inwardly from the sealing skirt body 48. The leaflets 110 are composed of bovine, equine, or porcine pericardial leaflets. The atrial sealing skirt 46 may be used as a docking system for any conventional valve, or may be pre-assembled to include valve 100 composed of leaflets 110. If the atrial sealing skirt 46 contains valve 100 composed of leaflets 110 sewn to the interior of the sealing skirt body 48, this configuration will function as any conventional valve does, with the leaflets 110 opening during diastole (relaxation of the heart) allowing blood to enter from the right atrium into the right ventricle, or from the left atrium into the left ventricle, and closing during systole (contraction of the heart), preventing blood from regurgitating from either the right or left ventricle back into the right or left atrium, respectively.

As shown in FIGS. 1-4, for example, the atrial sealing skirt 46, defined by atrial skirt body 48 and atrial skirt top brim 47, includes a membrane-like material and the sealing skirt 46 has a diameter greater than the annulus at the site of deployment. For example, the atrial sealing skirt 46 may have a skirt diameter greater than the diameter of either the tricuspid or mitral annulus. In another aspect, the atrial skirt is formed by, but not limited to, synthetic materials from the classes consisting of polycarbonate, polyurethane, polyester, expanded polytetrafluoroethylene (ePTFE), polyethylene terephthalate (PET), silicone, natural or synthetic rubbers, or a combination thereof. The atrial skirt 46 may also be covered with adult or juvenile bovine, ovine, equine, or porcine pericardium. Optionally, at least a portion of the atrial sealing skirt 46 may be formed from alternative materials, such as, for example and without limitation, polyurethane foam or other polymers.

In another aspect, at least a portion of the atrial sealing skirt 46 has one or more fixation members (not shown) along its length, allowing further anchoring to the right atrial floor and/or other portions on the atrial side of the tricuspid annulus, preventing migration of the atrial sealing skirt 46 into the proximal right atrium, thereby preventing instability (e.g. rocking) and paravalvular regurgitation of prosthesis. Optionally, with slight modifications, these fixation members permit further anchoring of the atrial sealing skirt 46 to the left atrial floor and/or portions on the atrial side of the mitral annulus, preventing migration of the atrial sealing skirt 46 into the proximal left atrium 8, also preventing instability (e.g. rocking) and paravalvular regurgitation of prosthesis.

The atrial sealing skirt 46 comprises at least an atrial skirt body 48 and an atrial skirt top brim 47. As shown, the atrial skirt body 48 is a cylinder and has a variable length and diameter. It is selectively composed of either laser-cut or molded nitinol, but also may contain elements of any other metallic alloy, and may be covered along any portion of its circumference or length with either biological membranes or synthetic materials mentioned above. As shown, the top brim 47 extends radially outwardly from the skirt body 48 and downwardly, forming a substantially concave top brim with the concavity facing the right atrial floor or left atrial floor. The brim 47 extends circumferentially around the upper end of the skirt body 48.

Figure 5:
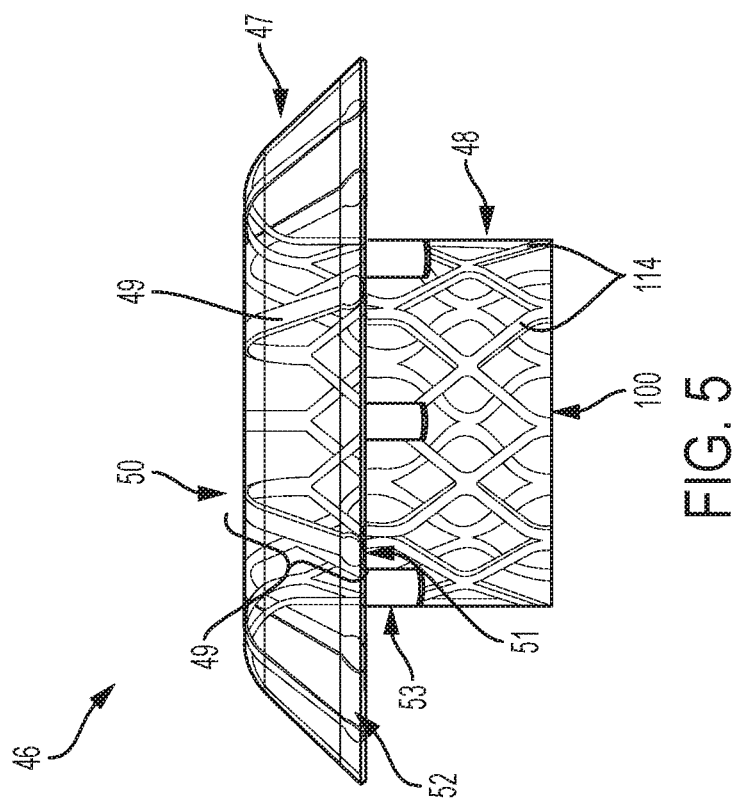
FIG. 5 is a side elevational of the atrial sealing skirt for receipt of a valve.

At least one, or shown a plurality of, flexible extension members 49 are provided and which may, for example, be composed of, but not limited to, laser-cut or molded nitinol attached to the top of the skirt body by the extension member base 50 and terminating in the extension member tip 51. Between one or more extension members 49, according to one aspect, is an elastic sealing membrane 52 extending perpendicular to adjacent extension members 49. As shown in FIGS. 5 and 6, the extension member 49 may extend radially outwardly and substantially linearly, but this is exemplary. As shown in FIGS. 1-4, the extension members may be nonlinear and generally U-shaped. As shown, the sealing membrane 52 extends circumferentially around the skirt brim 47. It may extend only a portion of the circumference as well. The sealing skirt body 48 includes a plurality of supports 114 which, like the extensions members 49 of the top brim 47, may, for example, be composed of, but not limited to, laser-cut or molded nitinol. As shown, the supports 114 form a lattice-like configuration, but other configurations are contemplated including, but not limited to, vertically extending supports.

Figure 9:
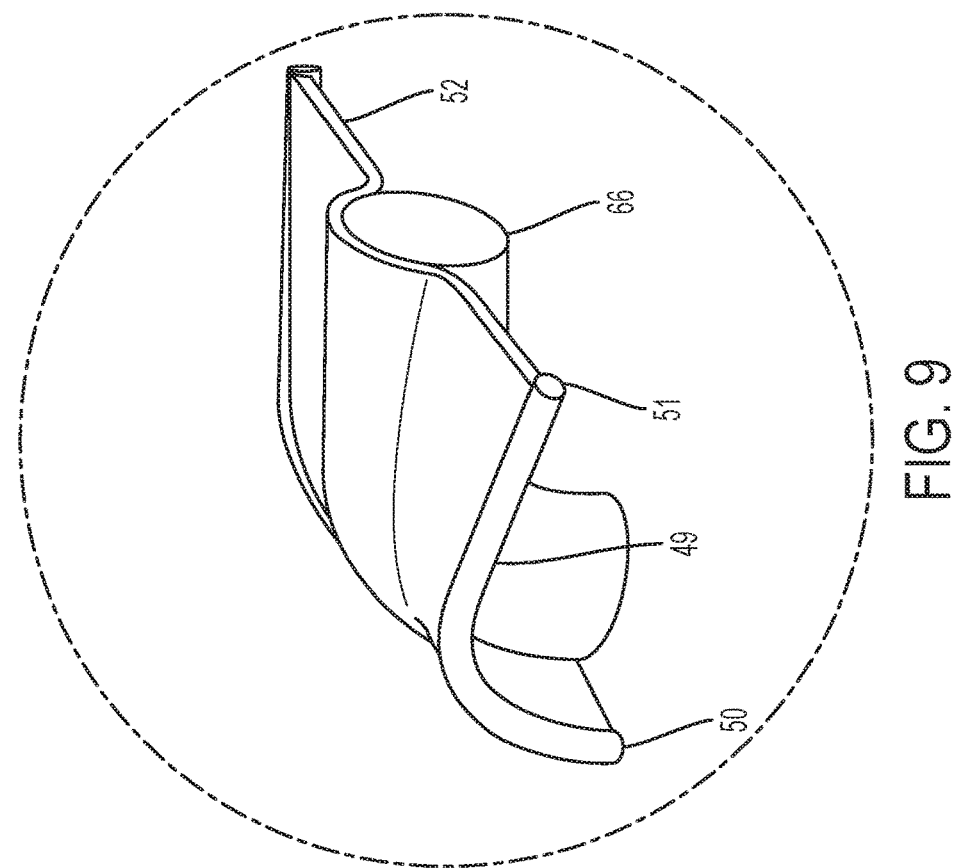
FIG. 9 is an enlarged perspective view of the atrial skirt conforming to and sealing around an intracardiac lead.

The sealing member 52, which is selectively provided, is composed of either biological tissues or synthetic fabrics as mentioned above. In one aspect, the synthetic fabric is either braided or knit, allowing the "stretchability" required to conform to atrial floor topography, including the ability to cover and seal intracardiac leads, such as permanent pacemaker leads 66 as shown in FIGS. 8 and 9. As shown in FIG. 9, the atrial skirt top brim 47 conforming to the right atrial floor 4 and sealing around intracardiac lead 66, according to one aspect. In FIG. 9, the extension member 49 is attached to the atrial skirt body 48 via the extension member base 50, and the extension member tip 51 is bending downwards, allowing the elastic sealing membrane 52 to wrap around the top of intracardiac lead 66, and thereby preventing regurgitation around the lead. This conformation requires downward force applied via one or more atrial positioning rods 44, attached to one or more conduits 53, and locked into place via one or more detachable locks 56 integrated inside the atrial end of the conduits 53 as described herein.

With reference to FIG. 7, the at least one atrial positioning rod 44 has a distal end 54, a proximal end 61 and an inner rod lumen 62 extending there between, the inner rod lumen being sized and configured so that a portion of a cord 21 or a member, such as a suture, connected to the cord, is inserted therethrough. At least a portion of the atrial positioning rod 44 is flexible so that the distal end 54 of the atrial positioning rod may be positioned at or adjacent to the deployment site. The at least one positioning rod 44 is coupled to the conduit 53. As illustrated FIGS. 10 and 11, each conduit 53 contains a detachable lock, which is configured to selectively secure at least one cord 21. Referring to FIGS. 10-14B, the locking system 55 consists of a detachable lock 56, integrated inside conduit 53, attached to first gateway hypotube 57 and second retracting hypotube 58. Inside the detachable lock 56 is a locking clip 59.

After the desired valve position is achieved, the at least one atrial positioning rod 44 urges the atrial sealing skirt 46 into position and is locked into place via a detachable lock 56 nestled within each conduit 53 and connected to the end of each positioning rod 44. The atrial sealing skirt 46 may be repositioned or retrieved until release of the cord 21 (or a member, such as a suture, extending therefrom) that extends through each atrial positioning rod 44

As shown in FIGS. 8 and 9, the positioning of the atrial sealing skirt 46 inside the right atrium so that the atrial skirt top brim 47 conforms to the topography of the right atrial floor 4 is shown. Via an atrial sealing skirt delivery system, the practitioner advances one or more atrial positioning rods 44 so that the atrial sealing skirt 46 translates over one or more cords 21, which extend through one or more conduits 53, defined by the atrial skirt body 48. As the atrial sealing skirt 46 advances toward the deployment site, the atrial skirt top brim 47 contacts the atrial floor 4, and the one or more extension members 49 flex differentially according to the local anatomy. Because each atrial positioning rod 44 is pushed with differential force, precise tension amounts are achievable, and therefore more or less flexion of the extensions members 49 to facilitate conformation of the atrial skirt top brim 47 around the entire perimeter of the atrial floor 4 to limit regurgitation through the tricuspid valve orifice.

Figure 15:
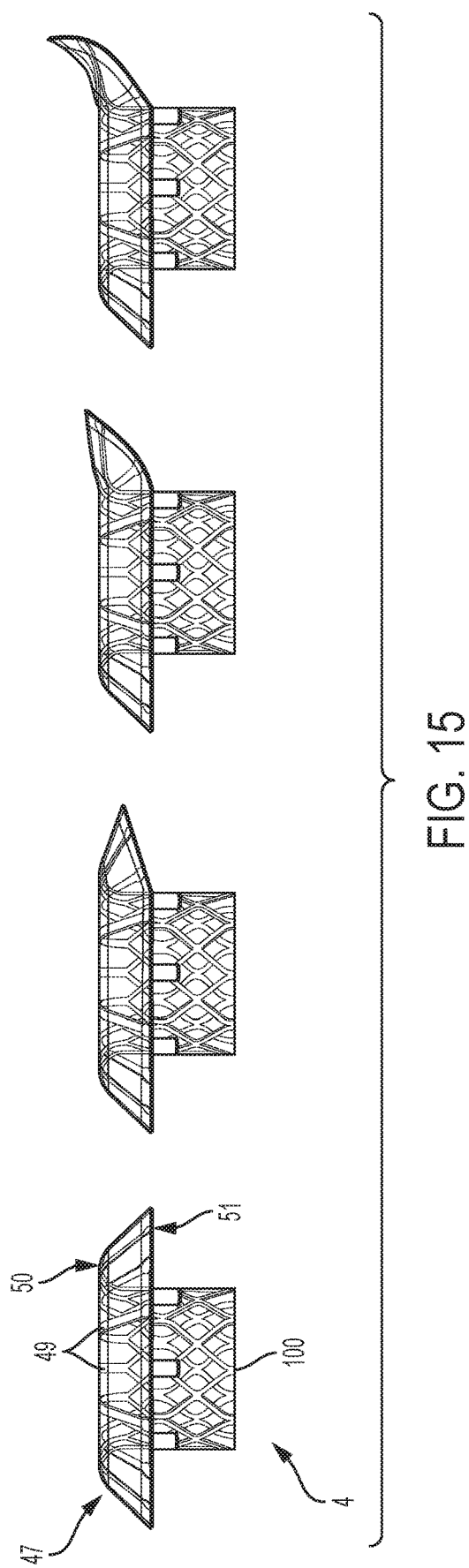
FIG. 15 is a series of side elevational views of the sealing skirt with one edge transitioning from a concave to a convex configuration.
Figure 16A:
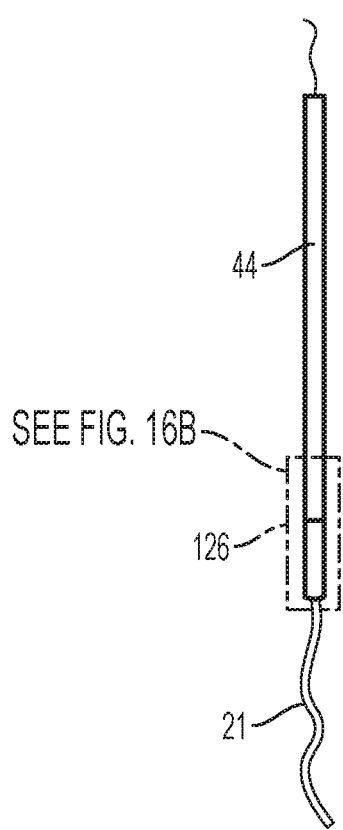
FIG. 16A is an elevational view of an atrial lock of the transcatheter valve system according to one aspect.
Figure 16B:
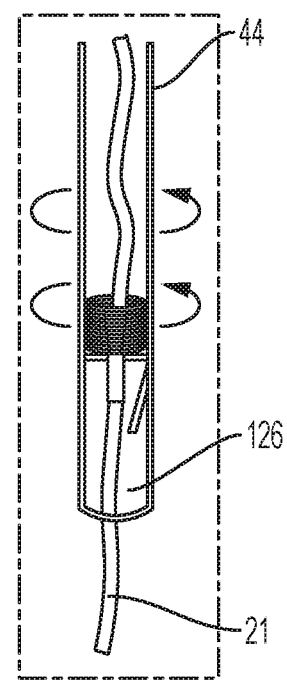
FIG. 16B is a magnified elevational view of the atrial lock of FIG. 16A.
Figure 18A:
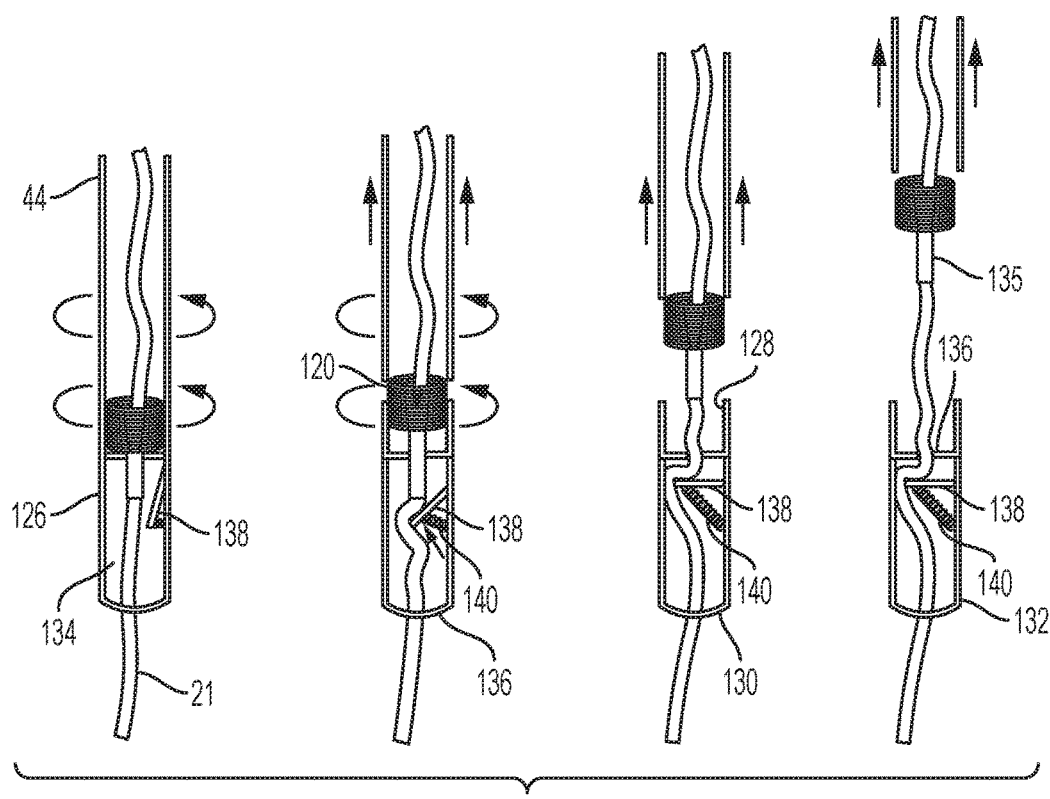
FIG. 18A is an elevational view of an atrial lock, according to one aspect.
Figure 18B:
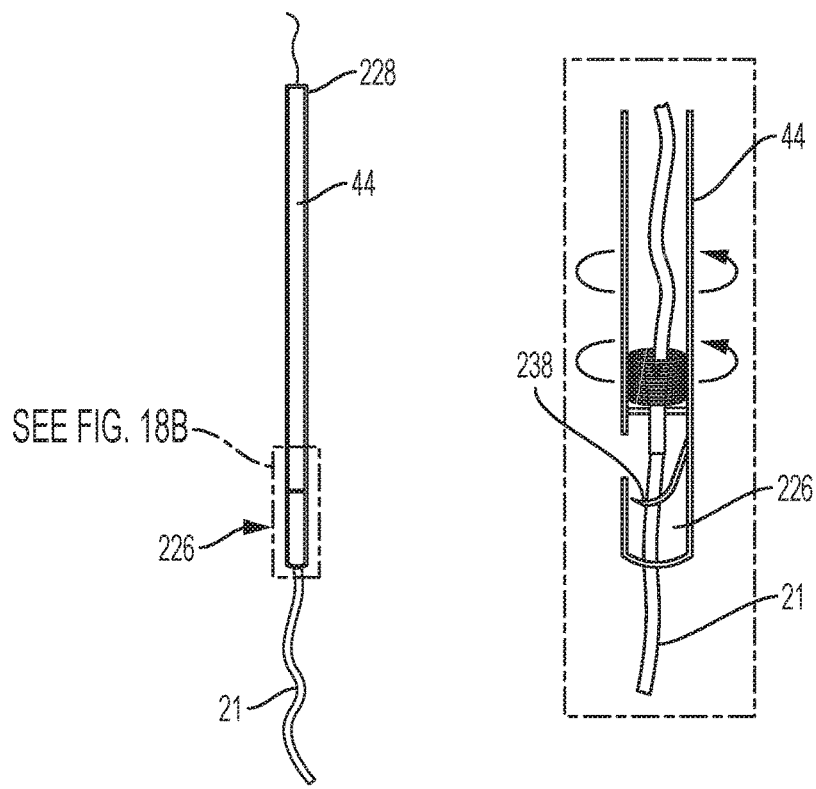
FIG. 18B is a magnified elevational view of the atrial lock of FIG. 18A.

FIG. 15 illustrates the conversion of the atrial skirt top brim 47 from concave to convex. As the valve is pushed down to the atrial floor 4 by atrial positioning rod 44, which is attached to the extension member base 50 of the extension member 49, the extension member tip 51 flexes upward, conforming to the convex atrial floor anatomy. Further distal movement of the positioning rod (shown left to right in FIG. 15) further modifies the shape of the sealing skirt 46 as it conforms to the atrial floor and as the extension member base 50 are urged downward by atrial positioning rod 44. By way of example only, the description of positioning and conforming of the atrial sealing skirt 46, as described above, refers to positioning of the atrial sealing skirt 46 onto the left atrial floor, thereby limiting regurgitation through the mitral valve orifice.

Now referring to FIGS. 13A and 13B, an inner surface of the lock 56 defines a first mating surface 133 which is shown as a threaded area. A distal end of the second hypotube 58 defines a second mating surface 134 configured to cooperate with the first mating surface 133. Accordingly, the second retracting hypotube 58 may be rotated so as to disengage the cooperating threaded areas 133 and 134. The second hypotube 58 is then retracted. This is illustrated in FIG. 13B. As the second hypotube clears (i.e., is withdrawn past) the tabs 64 of the first hypotube 57, the tabs 64 are biased inwardly to release the first hypotube 57 from the lock 56 to enable it to also be retracted. FIG. 14A illustrates the lock 56 after the first 57 and second 58 hypotubes have been retracted. Moreover, pulling of the retracting hypotube 58 causes retraction of locking clip 59, which pushes down on locking tabs 63, engaging cord 21. More specifically, the second hypotube 58 is retracted and due to its connection to the locking clip 59, it also retracts the locking clip 59. The locking clip 59, upon retraction, contacts the contact points 64 of the first gateway hypotube 57, disconnecting the clip 59 permitting the second hypotube 58 to be removed. Once retracting hypotube 58 is pulled, the inner arms of gateway hypotube 57 spring inward. The first gateway hypotube 57 beneficially enables the cord 21 to be locked while the second hypotube 58 is being retracted. Once the gateway hypotube 57 is removed, the clip 59 remains within the conduit 53 of the atrial sealing skirt 46. FIG. 14A shows a cut-away view of a lock fully engaged. According to one aspect, the positioning rod 44 may be integrated with the gateway hypotube or removably connected thereto. FIG. 14B shows an intact view of a fully engaged lock.

In one aspect, prior to release of the cord 21, the atrial sealing skirt 46 may be retrieved or repositioned. For example, if it is determined that the atrial sealing skirt is to be removed or repositioned, an atrial positioning rod 44 is positioned over each suture so that a portion of the suture 45 is in the inner rod lumen 62. When the distal end 54 of the positioning rod is adjacent to or in contract with the detachable lock 56, the first gateway hypotube 57 is advanced back into the lock 56, following by the second retracting hypotube 58, whose second mating surface 134 can screw back into first mating surface 133, allowing the second retracting hypotube 58 to push the first mating surface 133 (attached to locking clip 59) down, thereby disengaging locking tabs 63 from cord 21. With each cord unlocked, the valve may be removed from and/or repositioned in the deployment site 5.

In another aspect, the atrial sealing skirt 46 may be repositioned and/or removed days to weeks after valve deployment. In this aspect, the sutures are not cut, but wrapped around a spool or other wrapping device. This device is then attached to the valve on the atrial skirt top brim 47. Days after deployment of the valve and completion of the procedure, the spool/wrapping device may be re-captured, allowing un-wrapping and retrieval of the sutures. An atrial positioning rod 44 is then positioned over each suture 45 so that a portion of the suture is in the inner rod lumen 62. When the distal end 54 of the positioning rod is adjacent to or in contract with the detachable lock 56, the first gateway hypotube 57 is advanced back into the lock 56, following by the second retracting hypotube 58, whose second mating surface 134 can screw back into first mating surface 133, allowing the second retracting hypotube 58 to push the first mating surface 133 (attached to locking clip 59) down, thereby disengaging locking tabs 63 from cord 21. With each cord unlocked, the valve is removed from and/or repositioned in the deployment site 5.

FIGS. 16A, 16B and 17A-D illustrate another aspect of the detachable lock 126. In one aspect, the lock has a first end 128, an opposed second end 130 and a sidewall 132 that cooperate to define a central cavity 134. In another aspect, the first end is threaded and configured to matingly engage complementary threads on the distal end 120 of an atrial positioning rod 44. An opening 136 is defined in each of the first and second ends of the lock 126 so that a portion of the cord 21 extends through both openings and through the central cavity. In use, described more fully below, the detachable lock is selectively attached to the atrial positioning rod by rotating the rod 44 in a first direction, and the detachable lock 126 is selectively detached from the atrial positioning rod by rotating the rod 44 in a second direction that is opposed to the first direction.

In one aspect, the detachable lock 126 further comprises a clamp 138 movable about and between a first locked position, in which a portion of the clamp secures the cord 21 in the desired position, and a second unlocked position, in which the clamp does not secure the cord in the desired position. A biasing member 140 such as a spring and the like is configured to urge the clamp 138 to the first locked position. A tab 135 or other protrusion extending away from the distal end 120 of the atrial positioning rod 44 is configured to maintain the clamp in the second, unlocked position when the detachable lock is attached to the rod 44.

FIGS. 18A-20D illustrate another embodiment of a detachable lock 226. In one aspect, the lock has a first end 228, an opposed second end 230 and a sidewall 232 that cooperate to define a central cavity 234. In another aspect, the first end is threaded and configured to matingly engage complementary threads on the distal end 120 of the atrial positioning rod 44. An opening 236 is defined in each of the first and second ends of the lock 226 so that a portion of the cord 21 extends through both openings and through the central cavity. In use, described more fully below, the detachable lock is selectively attached to the atrial positioning rod by rotating the rod 44 in a first direction, and the detachable lock 226 is selectively detached from the atrial positioning rod by rotating the rod 44 in a second direction that is opposed to the first direction.

In one aspect, the detachable lock 226 further comprises an atrial anchor 238 movable about and between a first locked position, in which a portion of the atrial anchor secures the cord 21 in the desired position, and a second unlocked position, in which the atrial anchor does not secure the cord in the desired position. A biasing member 240 such as a spring and the like is configured to urge the atrial anchor 238 to the first locked position. A tab 135 or other protrusion extending away from the distal end 120 of the atrial positioning rod 44 is configured to maintain the atrial anchor in the second, unlocked position when the detachable lock is attached to the rod 44.

In one aspect, an anchor exit port 242 is defined in a portion of the sidewall 232 of the detachable lock 226. In this aspect, the anchor exit port is sized and shaped so that, in the first locked position, a hook 244 or other grasping element positioned on a tip of 246 of the atrial anchor extends through the port 242 and outside of the central cavity 234. In use, in the first locked position, the hook securely anchors the detachable lock (and thus, the cord 21) to a portion of the atrium 2.

In use, the assembly implants the sealing skirt 100 with a transcatheter approach by placing a right ventricular anchor first. The valve position would not require pulling a tether through an intracardiac wall such as the ventricular apex of the heart, because the sealing skirt 46 moves freely over the tether until the desired skirt 46 position is achieved. After the desired skirt 46 position is achieved, the at least one atrial positioning rod 44 urges the atrial sealing skirt top brim 47 into position and is locked into place via a detachable lock 126, 226 at the end of each positioning rod. The valve is repositioned or retrieved until release of the sutures 45 that extend through each atrial positioning rod 44.

Figure 21:
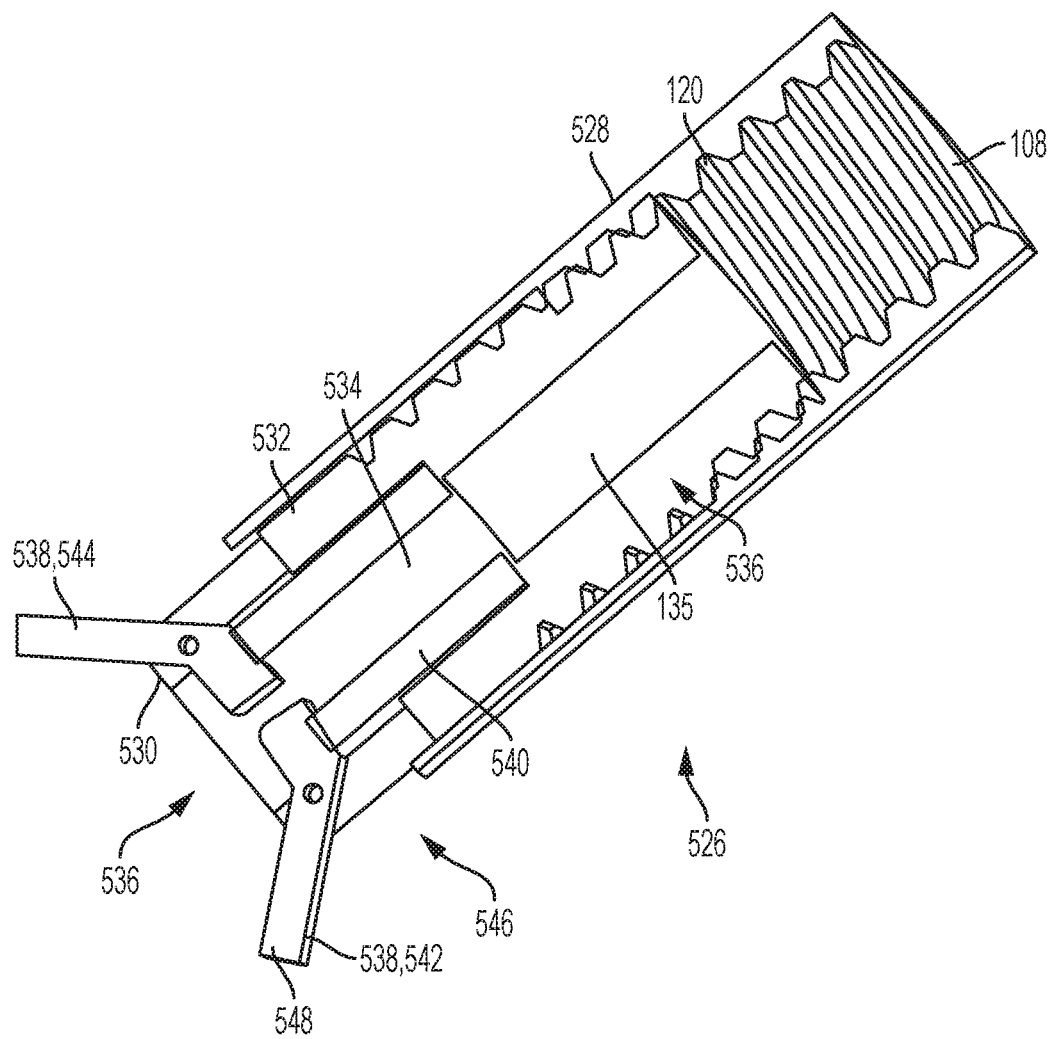
FIG. 21 is cross-sectional view of an atrial lock according to another aspect.

FIG. 21 illustrates another embodiment of a detachable lock 526. In one aspect, the lock has a first end 528, an opposed second end 530 and a sidewall 532 that cooperate to define a central cavity 534. In another aspect, the first end is threaded and configured to matingly engage complementary threads on the distal end of the atrial positioning rod 44. An opening 536 is defined in each of the first and second ends of the lock 526 so that a portion of the cord 21 extends through both openings and through the central cavity. In use, described more fully below, the detachable lock is selectively attached to the atrial positioning rod by rotating the rod 44 in a first direction, and the detachable lock 526 is selectively detached from the atrial positioning rod by rotating the rod 44 in a second direction that is opposed to the first direction.

In one aspect, the detachable lock 526 further comprises at least one atrial anchor 538 movable about and between a first locked position, in which a portion of the atrial anchor secures the cord 21 in the desired position, and a second unlocked position, in which the atrial anchor does not secure the cord in the desired position. Optionally, the atrial anchor comprises a first atrial anchor 542 and a second atrial anchor 544. In another aspect, the atrial anchor comprises a cam lever arm. A biasing member 540 such as a spring and the like is configured to urge the atrial anchor 538 to the first locked position. In a further aspect, the biasing member is a compressible polymer. A tab 135 or other protrusion extending away from the distal end of the atrial positioning rod 44 is configured to maintain the atrial anchor in the second, unlocked position when the detachable lock is attached to the rod 44.

In one aspect, an anchor exit port 546 is defined in a portion of the sidewall 532 of the detachable lock 526. In this aspect, the anchor exit port is sized and shaped so that, in the first locked position, a portion 548 of the atrial anchor 538 extends through the port 546 and outside of the central cavity 534. In use, in the first locked position, the atrial anchor securely anchors the detachable lock (and thus, the cord 21) to a portion of the atrium.

Although several aspects of the invention have been disclosed in the foregoing specification, it is understood by those skilled in the art that many modifications and other aspects of the invention will come to mind to which the invention pertains, having the benefit of the teaching presented in the foregoing description and associated drawings. It is thus understood that the invention is not limited to the specific aspects disclosed hereinabove, and that many modifications and other aspects are intended to be included within the scope of the appended claims. Moreover, although specific terms are employed herein, as well as in the claims that follow, they are used only in a generic and descriptive sense, and not for the purposes of limiting the described invention.

What is claimed is:

1. An atrial sealing skirt configured for receiving a valve and for endovascular introduction and implantation at a deployment site and configured and sized to replace a native heart valve, said atrial sealing skirt being configured to substantially conform to an atrial floor adjacent the atrial sealing skirt deployment site and comprising:
    an atrial skirt body which is generally cylindrical, and which defines a valve receptacle;
    an atrial skirt top brim extending circumferentially around an upper edge of said atrial skirt body, and wherein said atrial sealing skirt is compressible when constrained and expands when released from constraints;
    at least one conduit having an open upper end positioned below said atrial skirt top brim wherein said conduit extends distally below said atrial skirt top brim adjacent a side surface of said atrial skirt body;
    at least one extension member for supporting said skirt brim, said extension member having a base end adjacent said skirt body upper edge which extends outwardly substantially to an outer edge of said atrial skirt top brim;
    at least one body support for supporting said skirt body; and
    a membrane covering said at least one extension member and said at least one body support for forming the atrial skirt top brim and body.

2. The atrial sealing skirt according to claim 1 further comprising a valve within said valve receptacle.

3. The atrial sealing skirt according to claim 1 wherein said at least one extension member is non-linear.

4. The atrial sealing skirt according to claim 1 wherein said at least one extension member is a plurality of said extension members.

5. The atrial sealing skirt according to claim 1 wherein said at least one body support is a plurality of extension members forming a lattice-like structure.

6. The atrial sealing skirt according to claim 1 wherein said at least one conduit is at least two conduits.

7. The atrial sealing skirt according to claim 1 wherein said membrane is formed of a synthetic material.

8. The atrial sealing skirt according to claim 1 further comprising a lock positioned within said conduit to lock said atrial skirt top brim against the atrial floor wherein said lock is configured to be unlocked to permit repositioning of said atrial sealing skirt.

9. The atrial sealing skirt according to claim 8 wherein said lock defines a central lumen configured for receipt of a tether for securing said atrial sealing skirt.

10. The atrial sealing skirt according to claim 9 further comprising a first hypotube defining a central lumen and configured for receipt by said lock lumen and configured to cooperate with said lock.

11. The atrial sealing skirt according to claim 10 further comprises a second hypotube defining a central lumen and configured for receipt by said first hypotube.

12. The atrial sealing skirt according to claim 10 wherein said lock defines first cooperating surface and said first hypotube defines a second cooperating surface wherein said first and second mating surfaces cooperate to selectively retains said first hypotube within said detachable lock.

13. The atrial sealing skirt according to claim 8 wherein said lock has a first proximal end defining a threaded aperture and a distal end with a central cavity extending between said ends.

14. The atrial sealing skirt according to claim 13 wherein said lock further comprises:
  a sidewall defining said lock central cavity and defining an exit port on said sidewall; and
  an atrial anchor within said lock central cavity, said anchor having a first end extending inwardly from said sidewall and a second end wherein said anchor is moveable between a first locked position wherein said anchor extends through said exit port in said first locked position to selectively lock said cord.

15. The atrial sealing skirt according to claim 14 wherein said lock includes at least two of said atrial anchors, said lock sidewall defining at least two exit ports configured for receipt of said atrial anchors wherein forces applied to said atrial anchors extend said atrial anchors outwardly from said lock central cavity through said exit ports.

16. The atrial sealing skirt according to claim 8 wherein said lock further comprises a clamp within said central cavity wherein said clamp is moveable between a first locked and second unlocked position to selectively lock said cord.

17. The atrial sealing skirt according to claim 8 wherein said conduit comprises a sidewall and said lock is removable from said sidewall.

18. The atrial sealing skirt according to claim 1 wherein said atrial skirt top brim is generally concave prior to conformance with the atrial floor.

19. The atrial sealing skirt according to claim 1 wherein said conduit has a proximal portion adjacent said atrial skirt top brim and a distal portion extending below said atrial skirt top brim wherein said distal portion is at least equal to said proximal portion in length.

20. The atrial sealing skirt according to claim 19 wherein said distal portion extending below said atrial skirt top brim wherein said distal portion is greater than said proximal portion in length.

21. The atrial sealing skirt according to claim 1 wherein said conduit is supported by said skirt body.

22. The atrial sealing skirt according to claim 21 wherein said conduit extends parallel to and alongside said side surface of said skirt body.

23. The atrial sealing skirt according to claim 21 wherein said side surface of said skirt body is an exterior surface.

24. The atrial sealing skirt according to claim 1 wherein said conduit comprises a solid sidewall.

25. The atrial sealing skirt according to claim 1 further comprising a lock positioned within said conduit to lock said atrial skirt top brim against the atrial floor.

26. The atrial sealing skirt according to claim 1 wherein said membrane is formed of a biologic material.

27. The atrial sealing skirt according to claim 1 wherein said skirt top brim includes an aperture and said aperture defines said open upper end of said conduit.

28. The atrial sealing skirt according to claim 1 wherein said at least one conduit extends adjacent an outer side surface of said atrial skirt body.

29. A method of sealing a transcatheter valve around an intracardiac lead comprising the steps of:
  introducing an atrial sealing skirt configured for receiving a valve and for endovascular introduction and implantation at a deployment site and configured and sized to replace a native heart valve, said atrial sealing skirt being configured to substantially conform to an atrial floor adjacent the atrial sealing skirt deployment site and comprising an atrial skirt body which is generally cylindrical and which defines a valve receptacle and an atrial skirt top brim extending circumferentially around an upper edge of said atrial skirt body, and wherein said atrial sealing skirt is compressible when constrained and expands when released from constraints, at least one conduit having an open upper end positioned below said atrial skirt top brim adjacent a side surface of said atrial skirt body wherein said conduit extends distally below said atrial skirt top brim; at least one extension member for supporting said atrial skirt top brim, said extension member having a base end adjacent said skirt body upper edge which extends outwardly substantially to an outer edge of said atrial skirt top brim, at least one body support for supporting said skirt body, and a membrane covering said at least one extension member and said at least one body support for forming the atrial skirt top brim and body;
  positioning said atrial sealing skirt at the deployment site; and
  sealing said atrial skirt top brim along the atrial floor and around the intracardiac lead.

* * * * *